(12) United States Patent
Herr et al.

(10) Patent No.: US 8,961,766 B2
(45) Date of Patent: Feb. 24, 2015

(54) MICROCHANNEL GEL ELECTROPHORETIC SEPARATION SYSTEMS AND METHODS FOR PREPARING AND USING

(71) Applicant: Sandia Corporation, Albuquerque, NM (US)

(72) Inventors: Amy E. Herr, Oakland, CA (US); Anup K. Singh, Danville, CA (US); Daniel J. Throckmorton, Tracy, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/960,608

(22) Filed: Aug. 6, 2013

(65) Prior Publication Data

US 2013/0327633 A1 Dec. 12, 2013

Related U.S. Application Data

(60) Division of application No. 12/728,797, filed on Mar. 22, 2010, now Pat. No. 8,524,060, which is a continuation-in-part of application No. 11/893,684, filed on Aug. 16, 2007, now abandoned, which is a continuation of application No. 11/137,745, filed on May 24, 2005, now abandoned, which is a continuation-in-part of application No. 10/646,808, filed on Aug. 25, 2003, now abandoned.

(51) Int. Cl.
*G01N 27/447* (2006.01)
*G01N 33/543* (2006.01)
*G01N 33/561* (2006.01)
*B01L 3/00* (2006.01)

(52) U.S. Cl.
CPC .... *G01N 27/44747* (2013.01); *G01N 27/44791* (2013.01); *B01L 3/502753* (2013.01); *G01N 33/54306* (2013.01); *G01N 33/561* (2013.01)
USPC .......................... 204/452; 422/82.07; 600/312

(58) Field of Classification Search
USPC ............ 422/82.05, 82.07; 600/312, 321, 329; 204/450–452
See application file for complete search history.

(56) References Cited

U.S. PATENT DOCUMENTS

| 6,187,250 B1 * | 2/2001 | Champagne ................... 264/495 |
| 2003/0116437 A1 * | 6/2003 | Burns et al. ................... 204/453 |

* cited by examiner

*Primary Examiner* — J. Christopher Ball
(74) *Attorney, Agent, or Firm* — Dorsey & Whitney, LLP

(57) ABSTRACT

A micro-analytical platform for performing electrophoresis-based immunoassays was developed by integrating photopolymerized cross-linked polyacrylamide gels within a microfluidic device. The microfluidic immunoassays are performed by gel electrophoretic separation and quantifying analyte concentration based upon conventional polyacrylamide gel electrophoresis (PAGE). To retain biological activity of proteins and maintain intact immune complexes, native PAGE conditions were employed. Both direct (non-competitive) and competitive immunoassay formats are demonstrated in microchips for detecting toxins and biomarkers (cytokines, c-reactive protein) in bodily fluids (serum, saliva, oral fluids). Further, a description of gradient gels fabrication is included, in an effort to describe methods we have developed for further optimization of on-chip PAGE immunoassays. The described chip-based PAGE immunoassay method enables immunoassays that are fast (minutes) and require very small amounts of sample (less than a few microliters). Use of microfabricated chips as a platform enables integration, parallel assays, automation and development of portable devices.

5 Claims, 15 Drawing Sheets

MICROCHANNEL GEL ELECTROPHORETIC SEPARATION SYSTEMS AND METHODS FOR PREPARING AND USING

CROSS REFERENCE TO RELATED APPLICATIONS

This application is divisional application of prior co-pending U.S. patent application Ser. No. 12/728,797, originally filed Mar. 22, 2010 which is a continuation-in-part application of prior co-pending U.S. patent application Ser. No. 11/893,684, originally filed Aug. 16, 2007 and entitled "A Method for Providing a Gel Electrophoretic Separation System," which is a continuation of prior co-pending U.S. patent application Ser. No. 11/137,745, originally filed May 24, 2005 and entitled "Method and Apparatus for Electrophoretic Immunoassay," now abandoned, which is a continuation-in-part of prior co-pending U.S. patent application Ser. No. 10/646,808, originally filed Aug. 25, 2003 and entitled "Multidimensional Electrophoresis and Method of Making and Using Thereof," now abandoned, from which priority is claimed and which is herein incorporated by reference in its entirety.

STATEMENT OF GOVERNMENT INTEREST

This invention was made with Government support under government contract DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

1. Field of the Invention

Embodiments of the present invention generally relate to gel electrophoretic immunoassay, and more specifically to on-chip electrokinetic methods for performing immunoassays. These immunoassays are fast (minutes) and require very small amounts of sample (less than a few microliters). Use of microfabricated chips as a platform for the immunoassays enables integration, parallel assays, automation and development of portable devices.

2. State of the Art

There is a great demand for methods and devices for rapid detection of molecules of interest in applications such as medical diagnostics, environmental monitoring, biological defense and pharmaceutical research. For example, in medical diagnostics, detection and quantitation of biomarkers (proteins indicative of a disease state) in bodily fluids form the basis of diagnosis and treatment of many diseases such as cancer and HIV. Immunoassays are one of the most widely used and sensitive techniques for detection and quantitation of analytes such as viruses, peptides, polynucleotides, proteins such as toxins, antibodies, and cytokines, and other small molecules. Immunoassays are based on specific recognition and binding of a biological ligand to another molecule, the prominent example being binding of an "receptor" molecule to an analyte such as an antigen, where the receptor molecule may be any species having a specific binding affinity for another species. Reporter molecules may include but are not limited to polyclonal or monoclonal antibodies; a Fab, F(ab') 2, scFV, or small chain fragment; a peptide or a peptide nucleic acid; an aptamer; lectin; one or more small ligands; an antigen; an enzyme; an oligonucleotide; a deoxyribonucleic acid; a ribonucleic acid; biotin; and cellular receptor binding proteins. The generality of immunoassays stems from the fact that most analytes implicated in disease progression are either antigens or antibodies or are molecules against which an antibody can be generated by utilizing the immune system of a host animal. Typically either the antibody or the antigen, or in many cases a secondary antibody, is labeled with a signal-generating molecule, or "reporter" molecule, such as a fluorescent molecule, a chemiluminescent molecule, an enzyme, a quantum dot, biotin, or a spin-label, to transduce the binding event into a measurable signal.

A typical immunoassay, such as in Enzyme-Linked Immunosorbent Assay (ELISA), is performed using a solid surface to immobilize one of the binding components (antibody or antigen). Multiple subsequent incubations and washing steps are required to separate the bound from unbound species—allowing for detection of only those species that have bound. In a sandwich ELISA using a microtiter plate, the antibody to the antigen of interest is adsorbed to a solid surface, in this example the bottom of the microtiter plate well. The surface is then blocked to eliminate nonspecific binding in subsequent steps by adsorbing a protein such as bovine serum albumin, followed by aspiration and rinsing to remove the unbound protein. In the second step, samples containing the antigen are incubated with the solid surface and the nonspecifically bound antigen is removed by washing. In the third step, a second antibody, also specific to the antigen, which is conjugated to one enzyme or fluorescent reporter molecule, is added. The amount of labeled antibody and, hence, the antigen is determined by assaying for the enzyme or detection of a fluorescent signal.

There exist numerous variations of immunoassays. ELISA, as described above, requires separation or washing steps, the ELISA is classified as a heterogeneous immunoassay. Whereas homogeneous immunoassays are performed where there is no need to perform separation or washing before quantitation—a signal is generated only from the bound analyte-antibody complex.

The conventional immunoassays, ELISA being the predominant variation, take a long time (hours) to complete as there are multiple incubation and washing steps involved. These assays also involve many steps that either require extensive labor or if automated, need large and expensive robotic liquid-handling equipment.

There has been extensive commercial and research interest in developing immunoassays that are fast, can be performed in portable devices and require minute amounts of sample and reagents.

Microchip Analysis

Microfluidic chips for analysis of biological molecules have attracted significant attention recently as they offer a number of advantages including speed of analysis, portability, ability to multiplex, and potential for integration.

Microfluidic systems employ microfabrication technologies borrowed from the microelectronics industry to form a network of microchannels (1 μm-200 μm in width and depth) in common materials such as glass or plastic. Many biochemical processes such as mixing, dilution, concentration, transport, separation, and reaction can be integrated and automated in a single chip. The ability to make multiple channels, without additional cost or time of fabrication, enables as many as 96 or more analyses to be performed simultaneously. Another key advantage offered by these systems is that they require, and are capable of handling, a very small amount of sample and reagent for each process—a few tens or hundreds of nanoliters, volumes that are impossible to analyze in conventional microtiter plates or vials as they will evaporate in seconds and are nearly impossible to handle.

In the last few years, routine biochemical methods have been adapted to microfluidic platforms without loss in performance. In fact, in many instances, miniaturization improves the performance in addition to enabling high throughput operation using vanishing small amounts of a biological sample. Methods such as protein and DNA electrophoresis, chromatography, cell sorting, and affinity assays (e.g., immunoassays) have been adapted to microchips. The microfluidic assays are typically faster, use 100-1000 times lower sample and reagents, and offer better separation resolution and efficiency than their conventional counterparts.

Another advantage that miniaturization offers is the ability to integrate different biochemical processes and components required to perform them. A complex microfluidic chip contains multiple liquid reservoirs, fluid channels, and materials to perform such diverse tasks as filtering, pumping, valving, dialysis, separation, detection, and the like. Compared to larger fluid-handling and analysis systems, an integrated microfluidic chip performs these tasks much faster using smaller amounts of reagents and has the potential to be significantly cheaper if mass produced. Integrating functions at microscale also greatly reduce sample loss and dilution, potentially allowing detection of amounts not possible at larger scale operation.

Electrophoretic Immunoassays

As explained earlier, a typical immunoassay is performed using a solid surface to immobilize one of the components (antibody or antigen) with multiple subsequent incubations and washing steps to separate the bound from unbound species. However, conventional assay methods generally require long incubation periods (hours) and appreciable amounts of sample and reagents in order to obtain the desired response. Electrophoresis in microchannels has been demonstrated as an efficient means to separate an immune complex from reporter molecules. In such systems, an immune complex and a reporter molecule, such as a fluorophore, are separated based upon differences in charge-to-mass ratios. Specific advantages of microdevice-based separations relevant to electrophoretic-based immunoassays include the potential for shortened incubation times (as compared to solid-phase systems), simplified assay protocols as compared to the multiple wash and detection steps required for conventional immunodiagnostics such as ELISA, and device form-factors amenable to system integration and automation. Additionally, electrophoretic immunoassays eliminate the need to immobilize analyte on a solid surface, thus avoiding complexities associated with the solid-phase. Several groups have demonstrated microdevices as an elegant architecture for conducting integrated immunoassays (see for instances Chiem, N., et al., *Anal. Chem.* 1997, v. 69, pp. 373-378; Koutny, L. B., et al., *Anal. Chem.* 1996, v. 68, pp. 18-22; Qiu, C. X., et al., *Electrophoresis* 2001, v. 22, pp. 3949-3958; and Cheng, S. B., et al., *Anal. Chem.* 2001, v. 73, pp. 1472-1479).

Polyacrylamide Gel Electrophoresis (PAGE) Immunoassays on Chips: Advantage of Cross-Linked Gels—Integration, Higher Sample Loading To date, the capillary- or microchip-based immunoassays are performed in an open or surface-modified microfluidic channel and predominantly use electrophoresis as the basis of separation. The open-channel assays suffer from a number of disadvantages: 1) Attaining adequate species discrimination with electrophoresis-based immunoassays, however, can be difficult since large analytes such as antibodies and immune complexes are known to vary little in charge-to-mass characteristics. 2) Open channel electrophoresis also suffers from non-specific adsorption. Antibodies or analytes can adsorb to the walls leading to loss of sample as well as degradation in assay performance as the adsorbed molecules can significantly alter the flow in the channels. Various surface coatings, both covalent and non-covalent, have been developed to reduce non-specific adsorption but these coatings are not stable and lead to irreproducible results. Moreover, in most cases these coatings reduce but do not eliminate non-specific adsorption—leading to significant changes in the flow profile and hence, assay performance and reproducibility.

PAGE-electrophoresis through a porous sieving polyacrylamide, in the forms of sodium dodecyl sulfate-polyacrylamide gel electrophoresis (SDS-PAGE) and native PAGE, is a widely-used method for separation of proteins. At conventional scale, PAGE is performed in cross-linked polyacrylamide gels sandwiched between glass plates. Conventional PAGE takes hours to run, needs large amounts of sample and is hard to automate and integrate. As explained in commonly owned U.S. patent application Ser. No. 10/646,808 entitled "Multidimensional Electrophoresis and Methods of Making and Using Thereof", originally filed Aug. 25, 2003, and which is herein incorporated by reference, we have recently developed methods to implement slab gel electrophoresis in microchips. The major challenge in performing PAGE in a chip is the difficulty of placing solid cross-linked gels in micron-sized channels.

However, we have overcome these difficulties and herein describe and have elsewhere reported (Herr, A. E. et al., "On-chip Native Gel Electrophoresis-Based Immunoassays for Tetanus Antibody and Toxin," *Anal. Chem.*; v. 77(2), Jan. 15, 2005: pp. 585-590, and Herr, A. E. et al., "Photopolymerized cross-linked polyacrylamide gels for on-chip protein sizing," *Anal. Chem.*; v. 76(16), Aug. 15, 2004: pp. 4727-4733, both herein incorporated by reference) a new method for providing a polyacrylamide gel in a microchannel and conducting separation assays for a variety of proteins including TTC (tetanus toxin C-fragment), IL-2 (recombinant human interleukin-2), FGF (recombinant human fibroblast growth factor), and IGF (recombinant human growth factor-I).

By using ultra-violet (UV) light to initiate polymerization, porous polymers can be formed in the channels of a microchip. Moreover, because polymerization is initiated by UV-light, the channels can be photolithographically patterned. Using a mask, the polymerization is restricted to UV-exposed regions, and monomers from the unexposed regions are flushed after the irradiation step. This allows polymer to be cast selectively in separation channels, while injection channels and the detection window remain open. This allows for rapid and repeatable injection, easy clean up of injection arms, and more sensitive detection. The ability to photopattern will also facilitate multi-dimensional separation by enabling multiple separate stationary phases in a single chip. Electrolytes are incorporated into the monomer mix allowing for generation of electrokinetic flow immediately after polymerization. This obviates need of pumps to condition the channels by removal of excess solvent and monomers.

SDS-PAGE allows for excellent discrimination of species by size, but sodium dodecyl sulfate can disrupt fragile immune complexes, making quantization of these complexes nearly impossible. Non-denaturing PAGE techniques, both with and without a detergent, have been shown to retain the biological activity necessary for intact immune complexes, yet allow analyte discrimination. The ability to discriminate between antigen, antibody, and immune complexes based upon size, as well as charge-to-mass ratio, mitigates the sometimes poor resolution observed using non-sieving electrophoretic immunoassay techniques. Our PAGE immunoassay is superior to zone electrophoretic immunoassays in many respects: 1) high separation resolution due to low non-specific binding, 2) fast separations (seconds) using short length channels (millimeters) due to the high surface area of the gel, 3) ready tailoring of gel porosity for specific applications, and 4) spatial-localization of photopatterned polyacrylamide (useful in multiplexing and integration).

SUMMARY

In this work, we disclose a method of on-chip electrophoretic immunoassays for rapid and sensitive detection of protein levels in buffers and biological fluids such as spiked serum, whole saliva spiked and native, and gingival crevicular fluid samples. The on-chip immunoassays employ a native PAGE separation in lithographically photopatterned cross-linked sieving gels for detection and quantification of antibody and protein levels. Use of in situ fabricated polymer matrices in microfluidic devices further aid in the development of chip-based immunoassays.

DETAILED DESCRIPTION OF EMBODIMENTS OF THE INVENTION

Recombinant tetanus toxin C-fragment (the atoxic binding portion of the native tetanus toxin C-fragment, hereinafter TTC) and monoclonal anti-tetanus toxin C-fragment antibodies (anti-TTC) were purchased from F. Hoffmann-La Roche, Ltd. (Indianapolis, Ind.). The supplier reported molecular weight (MW) for the TTC was 50 kDa. ALEXA FLUOR® 488 fluorophores dye was obtained from Molecular Probes, Inc., (Eugene, Oreg.). Fluorescein isothiocyanate (FITC) labeled bovine serum albumin (BSA*, MW 66 kDa) was purchased from Sigma-Aldrich, Inc., (St. Louis, Mo.). Green fluorescent protein (GFP, MW 27 kDa) was purchased from Qbiogene Inc., (Montreal, Canada). Bovine serum was obtained from Sigma-Aldrich, Inc., and centrifuged at 6000 rpm for 20 minutes prior to use. While many photoinitiators can be employed, water-soluble photoinitiators 2,2'-Azobis (2-methylpropionamide)dihydrochloride (V-50), and 2,2'-Azobis[2-methyl-N-(2-hydroxyethyl)propionamide] (VA-086) were purchased from Wako Chemicals USA (Richmond, Va.). Solutions of 3-(trimethoxysilyl)propyl methacrylate (98%), 40% acrylamide, and 30% (37.5:1) acrylamide/bis-acrylamide were purchased from Sigma-Aldrich, Inc. Premixed 10× Tris-glycine ($25\times10^{-6}$ M Tris(hydroxymethyl) aminomethane, pH 8.3, $192\times10^{-6}$ M glycine) electrophoresis buffer was purchased from Bio-Rad Laboratories, Inc. (Hercules, Calif.). Deionized water (18.2 MΩ) was provided by a water purification system such as SYNERGY®, DIRECT-Q® or MILLI-Q® obtained from the Millipore Corporation (Milford, Mass.).

FITC and ALEXA FLUOR® 488 were used to fluorescently label or "tag" TTC using protocols found in product manual MP 00143 titled "Amine Reactive Probes" published by Molecular Probes Inc., and herein incorporated by reference. FITC was used for CCD imaging experiments, while ALEXA FLUOR® 488 was used in single point detection experiments. Fluorescently labeled TTC is hereinafter referred to as TTC*. FITC was abandoned in favor of ALEXA FLUOR® 488, as FITC was found to dissociate from the labeled proteins, resulting in variable fluorescent signals from the internal standard and the analyte. The final concentrations of TTC* stock solutions were measured using an absorbance method outlined by Molecular Probes (MP 06434, product insert for F-6434).

Chip Fabrication

Numerous microfabrication strategies, including fabrication of channels in fused silica, polymer devices, and hybrid devices such as silicon and glass are acceptable. For the work presented here, the microchips were fabricated from Schott D263 glass wafers obtained from the S. I. Howard Glass Co., (Worcester, Mass.). The wafers comprised a diameter of about 102-mm and a thickness of by 1.1-mm and were prepared using standard photolithography, wet etching, and bonding techniques as described previously by Throckmorton, et al., (*Anal. Chem.* 2002, v. 74, pp. 784-789), herein incorporated by reference. The chips contained offset double-T junctions. Separation channels measured either about 61-mm or about 67-mm in length, depending on the device used. The injection and buffer arms each measured about 5-mm in length. The channels were nominally 40 μm deep and 100 μm wide. To form buffer reservoirs, NANOPORT® assemblies from Upchurch Scientific (Oak Harbor, Wash.) were attached to through holes formed in the cover plate by using thermally cured adhesive rings.

In order to prepare the chip for separation analysis the silica microchannels were first cleaned, conditioned, functionalized using acrylate-terminated self-assembled monolayers (SAM's), and subsequently filled with linear polyacrylamide which is immobilized in a manner similar to that described by Kirby, et al., (see *Lab on a Chip* 2003, v. 3, pp. 5-10, herein incorporated by reference in its entirety) Singh, et al., (U.S. patent application Ser. No. 10/646,808 originally filed Aug. 25, 2003 entitled "Multidimensional Electrophoresis and Method of Making and Using Thereof", herein incorporated by reference in its entirety).

The microchannel cleaning was performed by flushing the channels with 1M NaOH for 10 minutes, followed by a 10 minute deionized water rinse, and a final filtered air purge. The conditioning step (to provide exposed acrylate groups on channel interior surfaces) comprised flushing the channels with a 2:3:5 mixture of 3-(trimethoxysilyl)propyl methacrylate, glacial acetic acid, and deionized water for 30 minutes. The conditioning mixture was prepared by vigorously agitating the solution while mixing the individual constituents, especially during the addition of the water, and then thoroughly degassing and sonicating the solution mixture for 5 minutes.

After the 30 minute conditioning step the channels were then purged with air and subsequently rinsed with deionized water for another 10 minutes.

To form the linear polyacrylamide channel coating (the SAM coating) within the channels, a solution of 5% (w/v) acrylamide containing 5 mg/mL V-50 was introduced into the channels. The filled channels were then exposed to a 100-Watt mercury lamp for 10 minutes, resulting in formation of the channel coating. The lamp was fan-cooled to minimize heating. Other fabrication procedures such as projection lithography (using a shaped laser light beam) have been employed to fabricate gel structures with high-spatial resolution (structures smaller than 20 um in width). Following the coating procedure, chips were flushed with deionized water for 5 min, filled with water and stored at 5° C.

Following surface preparation, polyacrylamide gels of various total acrylamide concentrations (monomer plus cross-linker) were fabricated in the microdevices. (NOTE: The acrylamide used to fabricate the sieving gel is a neurotoxin absorbed through the skin. Proper handling procedures are required. Users should consult the appropriate MSDS for proper safety precautions.)

The polyacrylamide gel matrix is formed by the co-polymerization of the two monomers: acrylamide and bis-acrylamide. The acrylamide polymerizes into long chains which are cross-linked at intervals by the bis-acrylamide thereby forming polyacrylamide. The porosity of the matrix can be altered by changing the percentage of acrylamide used and/or the amount of crosslinker bis-acrylamide present. The higher the percentage of acrylamide in a gel, the more dense the gel and the better the separation of small proteins. In contrast, the lower the percentage of acrylamide, the more open the matrix which favors the separation of larger proteins.

Polyacrylamide gel matrixes having various concentration of total acrylamide, T, (where T=4%, 6%, and 10%) were fabricated by adjusting the total volume of the 30% (37.5:1) acrylamide/bis-acrylamide solution with Tris/glycine run buffer gel containing 0.2% (w/v) VA-086 photoinitiator. As used herein, T, is expressed as a percentage of the total weight of acrylamide plus bis-acrylamide used to form the gel to the volume of the polymerized gel that is formed. Thus, a T of 6% would indicate that there is a total of 6 grams of acrylamide plus bis-acrylamide per 100 ml of gel. The amount of cross-linking can also be adjusted to vary the pore size.

Apparatus

Figure 1A:
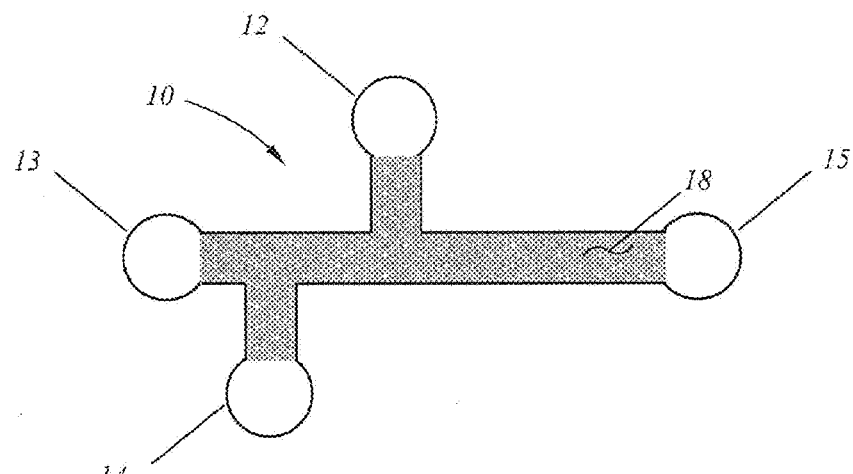
FIG. 1A illustrates a cartoon of the cross-linked polymer fabricated into unmasked regions of the microchannels.

The exemplary separation channel 10 in the microchip described above containing the immobilized polyacrylamide gel 18, is shown schematically in FIG. 1A. Sample introduction and separation were performed using common electrokinetic injection methods. The various sample, waste, and buffer reservoirs on a standard offset double-T microdevice were filled with 1× Tris-glycine/SDS run buffer. Sample reservoir 12 is filled with the sample solution (not shown) under analysis. Platinum electrodes (not shown) were inserted at each fluid reservoir 12, 13, 14 and 15 to provide electrical connectivity to a programmable high-voltage power supply (not shown). A typical voltage program was as follows: during sample loading, +300V/cm was applied between the sample and sample waste reservoirs for 240 seconds; separations were initiated by applying a positive high voltage at the buffer waste reservoir while grounding the buffer reservoir. No 'pullback' voltage was necessary during injection, as the high viscosity of the polymer matrix reduced leakage of sample from the loading arms into the separation channel.

Species transport was observed by using an epifluorescent microscopy technique and digital imaging, while laser induced fluorescence (LIF) and single point detection were used to obtain electropherograms and sensitivity data. Images were collected using an inverted epifluorescent microscope (IX-70, Olympus, Melville, N.Y.) equipped with 4× and 10× objectives (numerical apertures of 0.16 and 0.4, respectively). An x-y translation stage (Olympus, Melville, N.Y.) was used to position the chip and various associated fixtures relative to the imaging optics. Excitation light (Argon ion laser, 488 nm) was frequency modulated using a mechanical chopper (220 Hz modulation) and reflected off of a dichroic mirror (XF2010, New Focus, Inc, San Jose, Calif.) through the microscope objective lens that defined the detection point on the separation chip. A custom fixture mounted on a 3-axis translation stage allowed aligning and focusing the laser beam onto the separation channel. Excited fluorescence light was gathered, spectrally filtered through a 535 nm notch filter (XF3084) and spatially filtered through an iris before being directed into a HAMAMATSU® H5784 photomultiplier tube (PMT). The signal from the PMT was demodulated using a lock-in amplifier obtained from Stanford Research Systems (Sunnyvale, Calif.) and the generated data signal, in the form of the PMT light response over time, acquired by a computer interfaced to a National Instruments 6020E DAQPad data acquisition interface (Austin, Tex.). Data and system control was performed using an in-house program written in LABVIEW® (National Instruments) provided an output response in the form of an electropherogram.

Figure 1E:
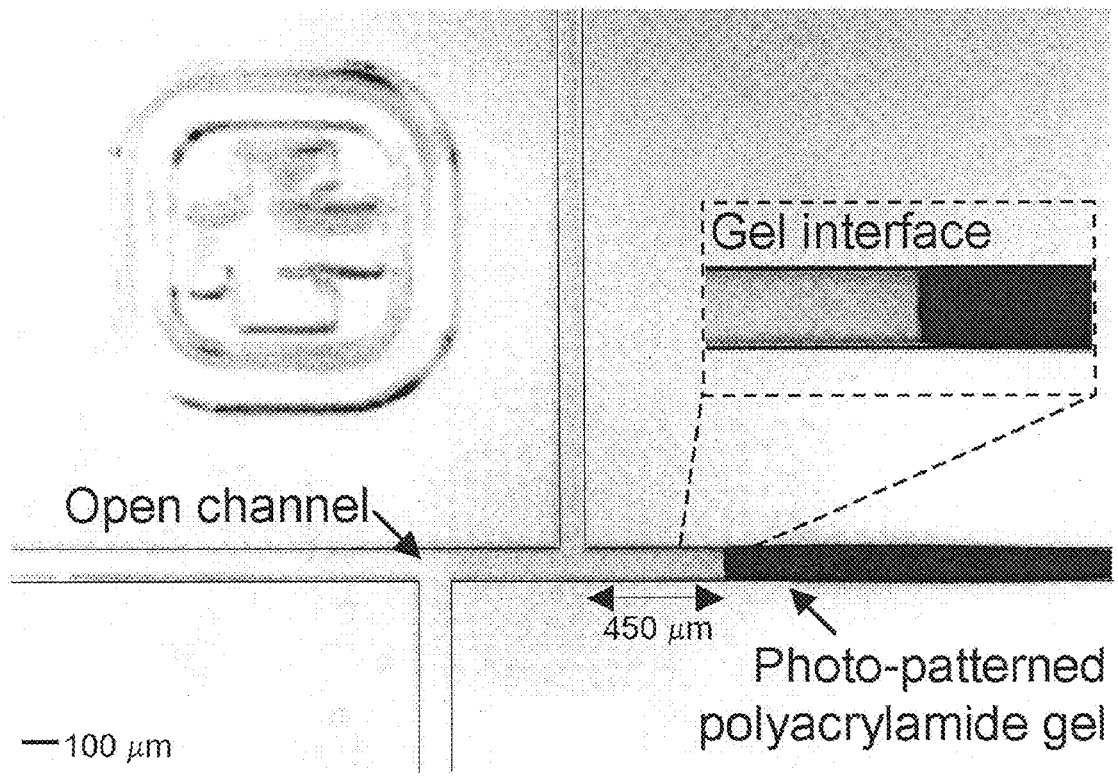
FIG. 1E shows an image of an actual microdevice that has been selectively patterned to incorporate a polyacrylamide gel matrix in a portion of one channel of a standard off-set T separation channel system.
Figure 1B:
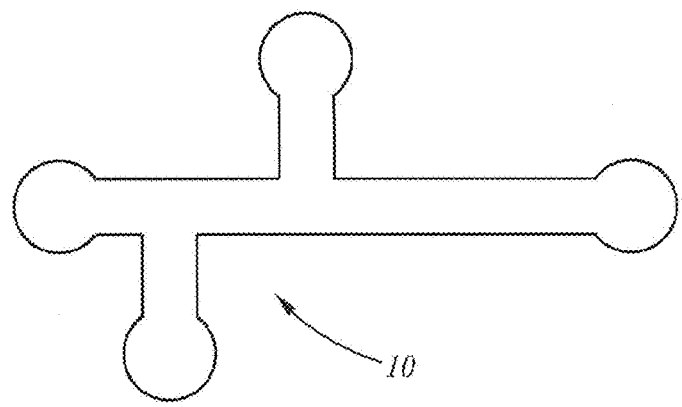
FIG. 1B shows a cartoon illustration of the cleaned and conditioned microchannels prior to filling and coating and immobilizing the polyacrylamide gel.
Figure 1C:
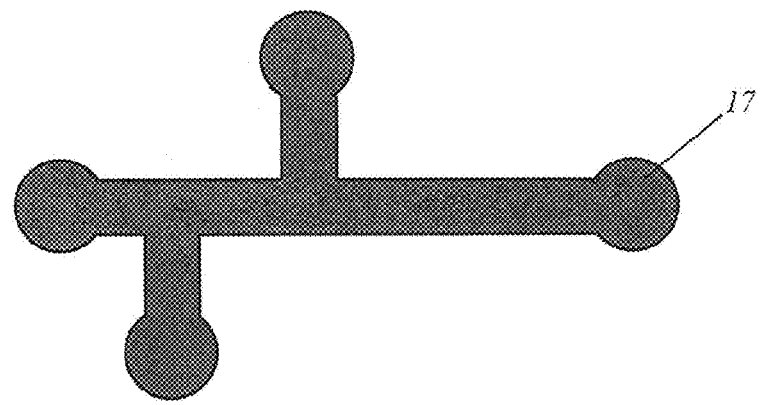
FIG. 1C shows a cartoon illustration of the microchannels flushed and filled with the acrylamide monomer/cross-linker solution.
Figure 1D:
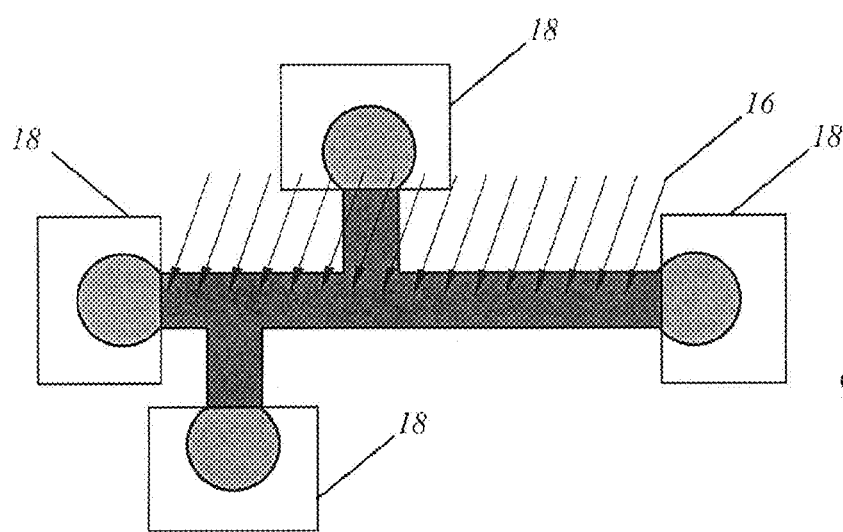
FIG. 1D shows the filled microchannels exposed to a UV source. Reservoirs are masked to prevent cross-linking of the monomer in these regions.

FIGS. 1B-1D schematically depict the polymer fabrication steps for the PAGE scheme of this embodiment. The separation system 10 shown in FIG. 1B, is shown filled in FIG. 1C with the unpolymerized acrylamide/cross-linked solution 17 using a low flow rate pressure-driven flow. In some instances, as shown in FIG. 1D, portions of the microdevice were masked using a UV blocking material 18 such as RUBYLITH® (Ulano Corp., Brooklyn, N.Y.) or electrical tape to prevent photo-polymerization of the gel. Polymerization was effected by exposing the channel structure to UV light 16 supplied by a 4-Watt illumination source (not shown) having a wavelength, λ, equal to about 365 nm for about 15 minutes. FIG. 1A show the resulting polymerized gel 18 contained within the channel device 10.

It was found that thoroughly degassing the polyacrylamide gel solution and using a low flow rate channel-filling protocol were essential to obtain high quality polymerized gels. Moreover, an additional 3 minutes of UV exposure were required for full polymerization of gel-filled channels near multiple inlet channels (i.e., regions near a "T" junction). Voids or "tears" formed near the offset double-T junction upon application of an electric field if this extended photo-polymerization step was omitted. The tears may arise from stresses induced by electroosmotic flow in channels filled with a non-uniformly polymerized gel. Chips containing polyacrylamide structures were stored submerged in buffer solution and refrigerated at 5° C.

FIG. 1E shows an image of a microdevice that has been selectively patterned to incorporate a polyacrylamide gel matrix in a portion of one channel of a standard offset T-separation channel system. However, while confinement of the polyacrylamide gel to a single channel (the separation channel) offers advantages when conducting either SDS or native PAGE analysis of a sample mixture, the presence of a polymer matrix in all channels of the device resulted in improved device performance for the immunoassays presented in this work. Therefore, all data presented in this work comprising PAGE analyses of both free and immune-complexed species were obtained from systems with polyacrylamide gel fabricated uniformly in all channels.

Best Mode

Figure 2A:
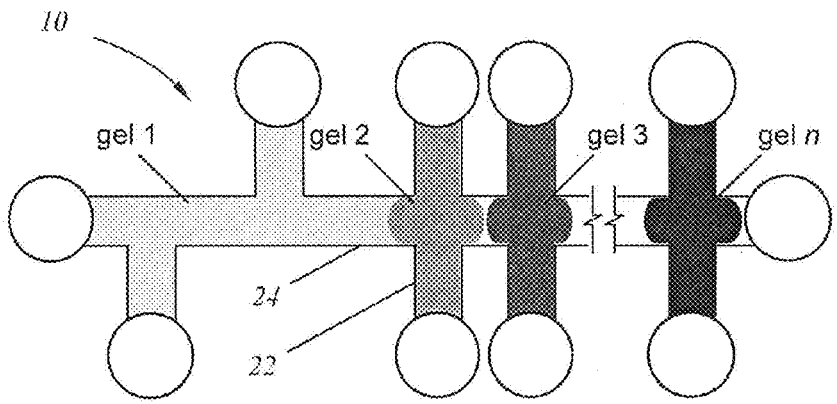
FIG. 2A shows an example of a fabrication method for loading various acrylamide solutions within a microchannel thereby providing a means for preparing a separation structure having a pore size that varies in a step-wise manner.
Figure 2B:
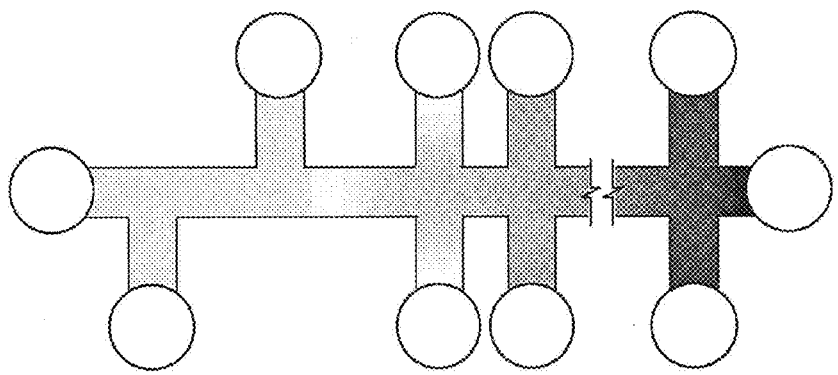
FIG. 2B depicts the microchannel of FIG. 2A after some incubation time that allows the various acrylamide solutions present in the device to diffuse into each other to provide an unpolymerized solution having a spatially-varying total acrylamide concentration along the length of the horizontal separation channel.
Figure 2C:
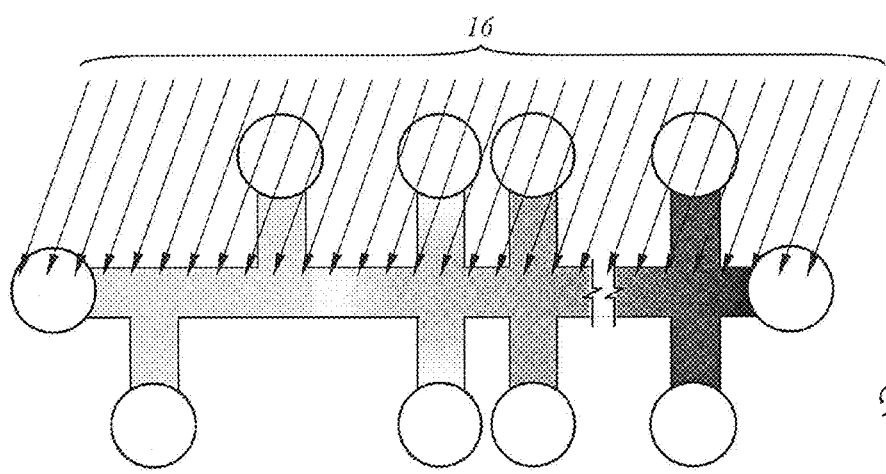
FIG. 2C shows the photo-polymerization step for this providing the polyacrylamide gel filled device.
Figure 2E:
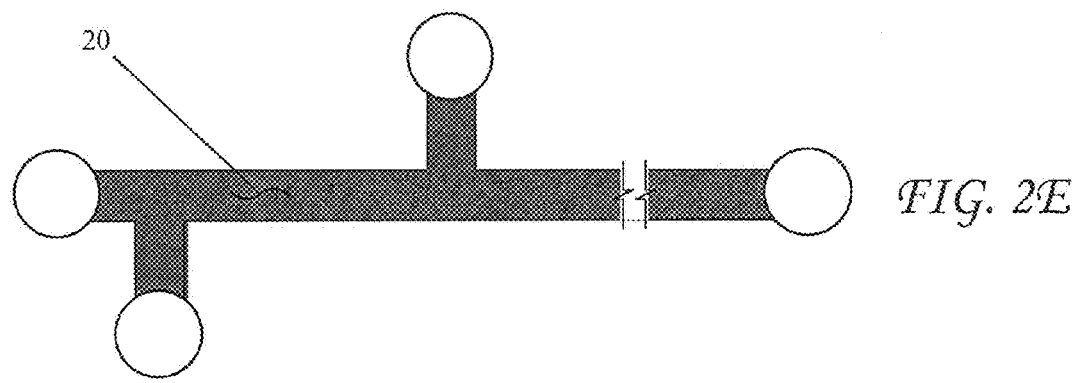
FIG. 2E shows the initial step of an alternative fabrication sequence for providing a polyacrylamide structure having a continuously varying pore size, wherein a single acrylamide solution having a first total acrylamide concentration is initially introduced into the separation channel.
Figure 2F:
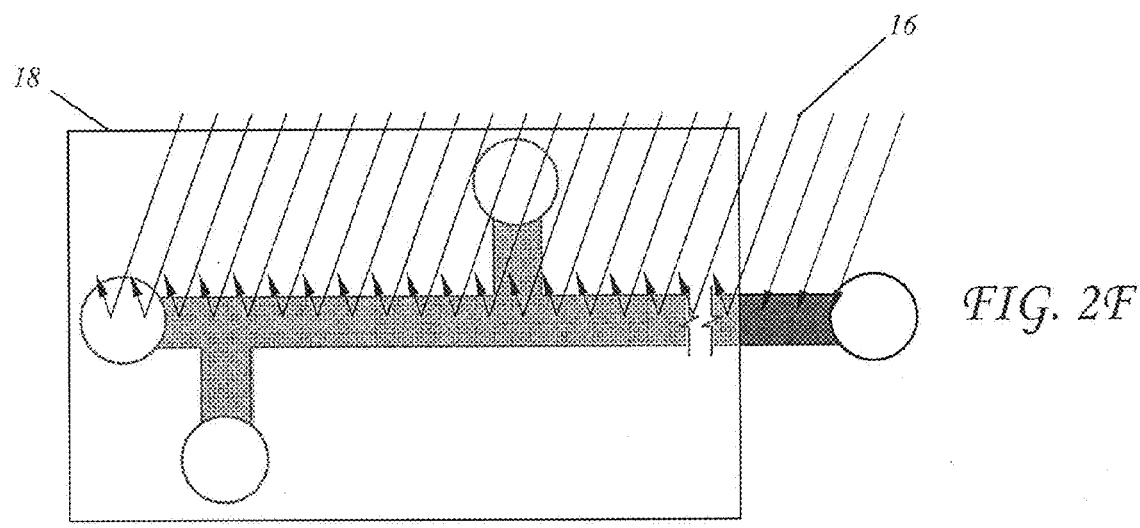
FIG. 2F shows the alternate process continuing by polymerizing an end region of the acrylamide solution by UV photopatterning resulting in a polyacrylamide gels terminal plug having a first pore size.
Figure 2G:
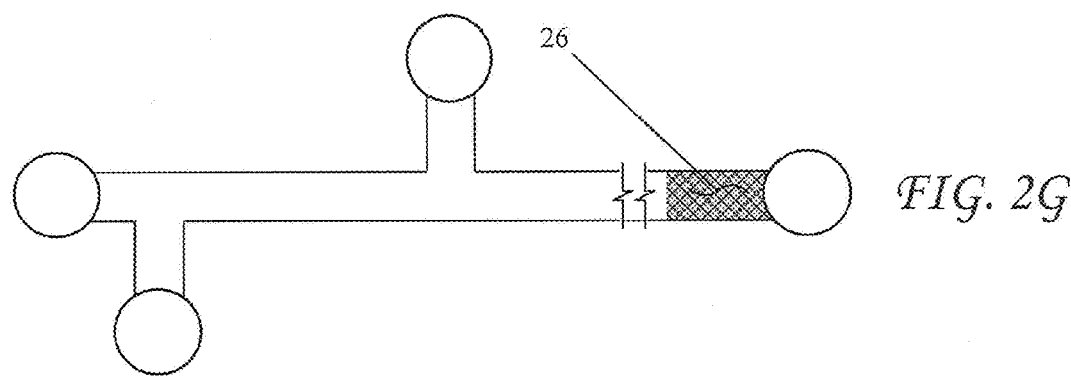
FIG. 2G depicts a subsequent step wherein a portion of the first (unpolymerized) acrylamide solution has been flushed out of the separation channel and replaced with a second acrylamide solution having a second total acrylamide concentration.
Figure 2H:
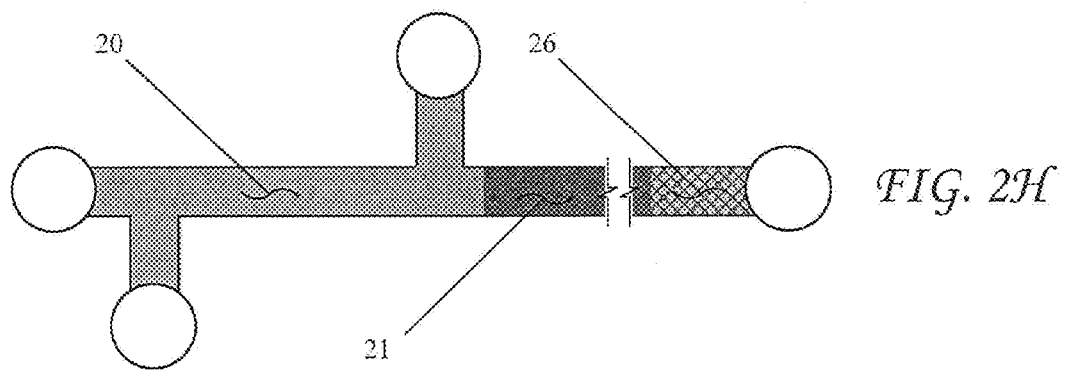
FIG. 2H depicts a time period in which the two unpolymerized solutions (new acrylamide solution and the original acrylamide solution that has been trapped in the channel) are allowed to diffuse, thus establishing a monotonically varying total acrylamide concentration within the separation channel.
Figure 2I:
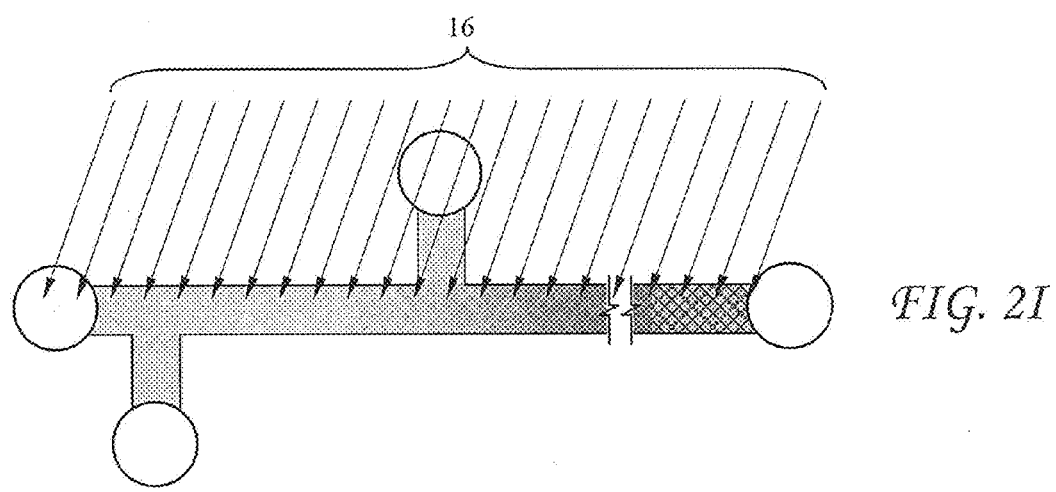
FIG. 2I shows photopatterning of the mixed acrylamide solution along the entire length of the separation channel.
Figure 2J:
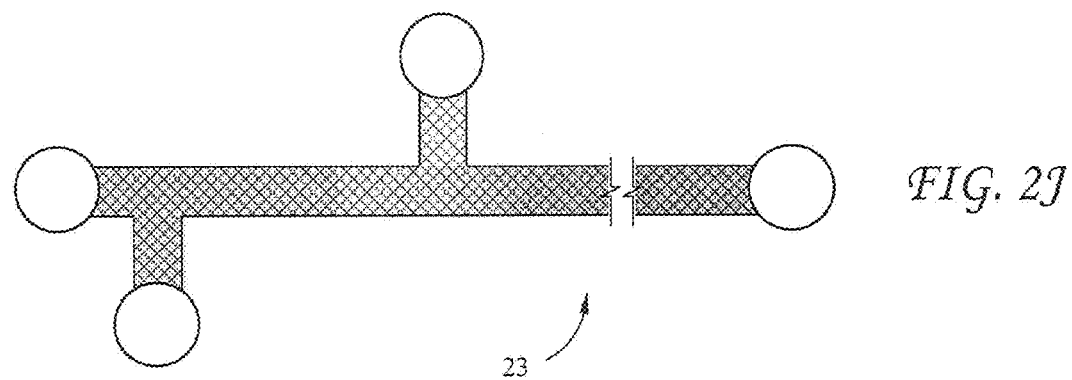
FIG. 2J depicts the final device wherein a continuous gradient in pore size has been fabricated in the horizontal microchannel.
Figure 2D:
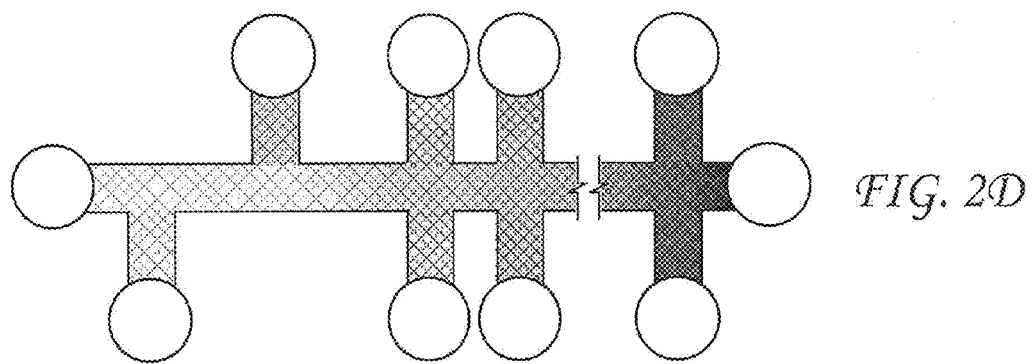
FIG. 2D shows a completed microchannel structure containing a polyacrylamide gel having a continuously varying pore size within the horizontal separation channel to form a complex configuration of multiple gel regions having a single loading structure.
Figure 2K:
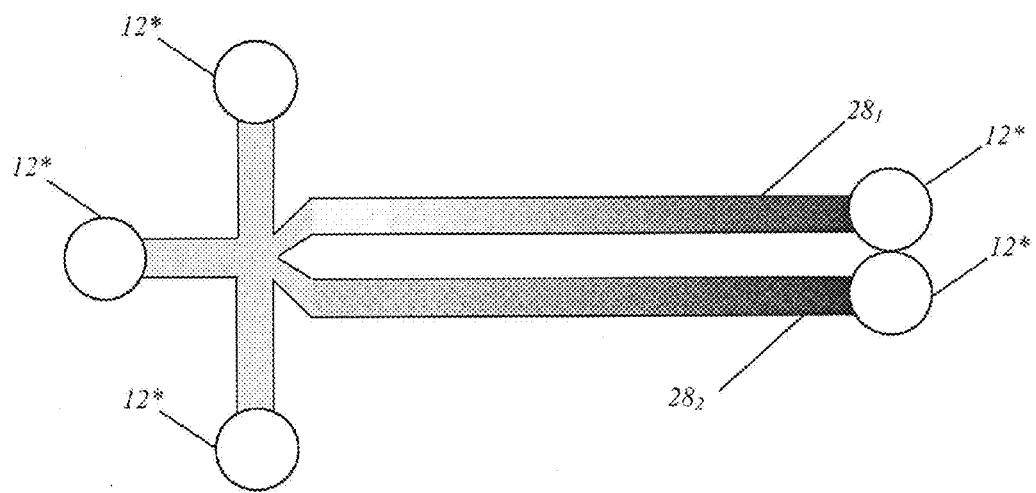
FIG. 2K provides an example of such a microdevice having various polyacrylamide gel characteristics localized in different regions of a single, multiple channel device.

In preferred embodiments, the device of the present invention comprises either a single separation channel, as depicted in FIGS. 2A-2J, or several separation channels attached to a single loading structure, as depicted in FIG. 2K, wherein each channel has a different set of gel pore properties.

FIG. 2A shows a first example of a method to fabricate a separation channel, wherein the pore size within the separation channel varies in a semi-continuous or continuous manner. In a design where multiple side-branching access channels 22 intersect the separation channel(s) 24, such access channels can be used to introduce any of several different unpolymerized gel solutions, 1, 2, . . . n, wherein each contains a different concentration of total acrylamide. In FIG. 2A, all access channels are loaded such that the separation channel is comprised of regions containing a different unpolymerized solution.

The separation channel thus prepared may be photopatterned using UV illumination in order or some amount of time to elapsed after introducing unpolymerized gel solutions, 1, 2, . . . n such that the different solutions are able to diffuse into each other. In this way the former embodiment now provides a separation channel containing a polymerized gel having a pore structure that varies in either a semi-continuous or a step-wise manner. In the second embodiment the polymerized gel comprises a structure whose pore sizes varies continuously within the separation channel(s).

In both embodiments the unpolymerized solution is photopatterned using UV illumination 16 as shown in FIG. 2C. This results in a gel structure having a variable pore size determined by the total acrylamide concentration of the unpolymerized solution(s) at each point along the length of the separation channel. Moreover, the overall length of time the solution is allowed to equilibrate will affect the final character of the pore size gradient.

A second example of this technique is used to fabricate a continuously varying pore size gradient by first filling the entire separation channels) with a single acrylamide monomer and cross-linker solution (the unpolymerized gel solution 1) 20 as shown in FIG. 2E. However, as depicted in FIG. 2F in the present example, only a portion of the separation channel, several channel widths from the intersection, is exposed to the UV light 16, while the remainder is blocked by UV blocking material 18 allowing for the definition of an end or terminus portion 26 of the pore size gradient as is depicted in FIG. 2G. Subsequently, a different monomer solution is introduced using a channel network by first removing some or all of solution 20 and re-introducing two or more solutions (e.g., solutions 20 and 21) as is depicted in FIG. 2H.

Again, a period of equilibration is provided, as shown in FIG. 2H, which allows the unpolymerized solutions, trapped in the separation channel due to the polymerized plug terminus, to diffuse into each other and thus establishing a continuous variation in the unpolymerized solution composition along the length of the separation channel.

After the desired equilibration period has elapsed, the entire separation channel is again exposed to UV light 16, as shown in FIG. 2I thereby providing the final polyacrylamide gel structure 23 having a gradient in pore size, as depicted in FIG. 2J.

TABLE 1, below, shows measurements of analyte mobility, in this case several different proteins, made at two different locations in the channel (gel regions 1 and 2, located at 2 mm and 3 mm from the loading channel respectively), in a gradient gel fabricated as described in FIGS. 2E-2I. Migration of each protein was imaged using an epi-fluorescence digital imaging technique. Frame-to-frame migration was used to calculate analyte velocity. With the known applied electric field, 320 V/cm, species mobility was calculated. Two regions were investigated to provide information on analyte mobility: imaging at 2 mm from the injection junction (region having larger pore size) and 3 mm from the injection junction (region having smaller pore size). Preliminary data show significant changes in the measured mobility, depending on which region of the device the species were migrating through. As shown in TABLE 1 the largest species (Proteins 2-5) had a mobility that was more significantly impacted than did the smallest species (Protein 1), as would be expected.

TABLE 1

| | Mobility × $10^5$, $cm^2/Vs$ | | Mobility change |
|---|---|---|---|
| Analyte | Gel region 1 (2 mm) | Gel region 2 (3 mm) | % reduction in mobility |
| Protein 1 | 3.0 | 2.5 | 17 |
| Protein 2 | 5.6 | 3.4 | 39 |
| Protein 3 | 7.8 | 4.9 | 38 |
| Protein 4 | 10.8 | 7.2 | 33 |
| Protein 5 | 13.6 | 9.2 | 33 |

Protein mobility measurements in two regions of a gradient separation gel.

Lastly, FIG. 2K shows two parallel horizontal separation channels $28_1$ and $28_2$, each having a different gel concentration gradient. Reservoirs 12* may or may not contain electrodes. If used, electrodes would be immersed in the liquid contained within the reservoir and preferably comprise a thin platinum wire or a patterned thin film of gold on the substrate wafer (not shown).

The polyacrylamide gels proved to be durable under limited current, limited field strength operation. Several individual chips were successfully used for hundreds of separations (each separation lasting 5-7 min), when the current flow was limited to ~10 mA and applied field strengths limited to ~410 V/cm. A few chips (five) were successfully employed for native PAGE immunoassays for several hours over several months of use. The mode of polymer failure has not been fully characterized. In agreement with published reports of in situ polymerized gel structure failure modes, a drop in the electrical resistance of the gel-filled microchannel correlated well with gel failure. In the gels presented in this work, failure manifested itself through the formation of visible voids in the bulk of the polymer.

In order to characterize the native PAGE performance of in situ photopolymerized polyacrylamide gels, apparent mobility measurements were made using three model proteins (GFP, BSA*, and TTC*) each transiting one of several different polyacrylamide gel concentrations while subjected to a variety of different applied electric field strengths. Species mobilities (µ) were calculated from the known applied field strength, the measured frame-to-frame displacement of each species, and the time between frames. No obvious dependence of apparent mobility of TTC* on field strength was observed for field strengths ranging from 245 V/cm to 410 V/cm. Additionally, GFP, BSA*, and TTC* showed a linear dependence between peak motion and time for all field strengths (245 V/cm to 410 V/cm) and gel concentrations (4%, 6%, and 10%) considered (n=27; $R^2 \geq 0.982$).

TABLE 2 details the apparent mobilities for the native proteins moving under the influence of an electrophoretic field in gels of various polyacrylamide concentrations. All three protein species exhibited a marked decrease in apparent mobility as polyacrylamide concentration increased. The observed trend indicates that the separation mechanism consists of both an electrophoretic component and a "sieving" component due to the gel pore size (expected to decrease as polyacrylamide concentration increases). Ferguson analysis can be employed to relate the polyacrylamide gel concentration to the measured apparent mobility of a protein through the retardation coefficient, $K_r$. A plot of the natural logarithm of µ versus polyacrylamide concentration yields $K_r$, as reported in TABLE 2. $K_r$ values reported by Gonenne and Lebowitz (*J. Anal. Biochem.* 1975, v. 64, pp. 414-424) for similar size native proteins, agree within 25% with those reported in TABLE 2 below.

TABLE 2

| | Mobility µ × $10^5$ $cm^2/Vs$ | | | Retardation Coefficient |
|---|---|---|---|---|
| | 4% Gel | 6% Gel | 10% Gel | $K_r \times 10^2$ |
| GFP | −10.8 ± 1.9 | −7.7 ± 0.3 | −4.4 ± 0.1 | 15.0 |
| BSA | −12.4 ± 0.4 | −10.3 ± 0.2 | −4.0 ± 0.3 | 19.5 |
| TTC | −3.9 ± 0.9 | −3.1 ± 0.9 | −1.8 ± 0.1 | 13.5 |

Native protein migration characteristics. Error is reported as a standard deviation (n = 4 to 22).

Separation resolution (SR) for an internal standard (in this case free FITC dye) and TTC* was employed to further characterize the native PAGE behavior of 4% and 6% acrylamide gels at a range of applied electric field strengths (ranging from about E=245 V/cm to about E=410 V/cm). Using the relation:

$$SR = \Delta L / 4\sigma_{avg},$$

where ΔL is the peak-to-peak distance and $\sigma_{avg}$ is the average width (1 standard deviation) of the two concentration distributions. SR was calculated by a least-squares Gaussian fit to image data (axial intensity distributions) at a set elapsed separation time ($\Delta t_{sep}=5s$). SR showed a linear proportionality to $\sqrt{E}$ for both the 4% (SR=$0.45\sqrt{E}-5.8$, $R^2=0.98$) and 6% gels (SR=$0.16\sqrt{E}-1.4$, $R^2=0.90$) over the range of electric field strengths (E) investigated. As expected, SR was markedly higher in the 6% acrylamide gel than in the 4% acrylamide gel for all E investigated. Observed mobility and SR dependence on polyacrylamide concentration indicates that the gel characteristics can be readily tailored to satisfy assay resolution requirements.

EXAMPLES

Example 1

On-Chip Direct Immunoassay for Anti-TTC Antibodies

Tetanus neurotoxin is produced by the anaerobic bacterium *Clostridium tetani* and is one of the most toxic substances known. The toxin binds to nerve cells and penetrates the cell cytosol where it blocks the release of neurotransmitter resulting in spastic paralysis.

Vaccination has proven to be the most effective intervention method for protecting human populations from tetanus and many other infectious agents. However, the efficacy of these vaccines against these agents must be determined objectively, typically by measuring the concentration of antibodies in serum known as an immunoassay. Conventional immunoassays such as ELISA are commonly used to measure concentrations of toxins in clinical samples or to assess antibody response to vaccination. Herein we report a microchip immunoassay for detection of tetanus antibody in buffer and diluted bovine serum.

Samples of TTC* and anti-TTC antibody having a known concentration were prepared in a 1× native Tris-glycine buffer, as well as in a diluted bovine serum solution. To perform direct immunoassays for anti-TTC antibodies, the initially prepared concentration of TTC* was held constant among samples while the volume of anti-TTC antibodies was varied within each sample to obtain the desired concentration of antibody in the final sample. All samples were adjusted to a final volume of 50 mL through addition of 1× native Tris-glycine buffer (or bovine serum). Samples were mixed by gently aspirating the sample through a pipette. Samples were then shielded from light and incubated in plastic tubes at room temperature for at least one hour. The immunoassays were conducted without boiling and without the inclusion of SDS in the sample in order to avoid protein denaturation and breakdown of antibodies into heavy and light chains.

The samples thus prepared were injected into the sample reservoir of the on-chip microsystem prepared as described above and comprising one of a variety of polyacrylamide gel concentrations and launched into the separation column under the influence of an electrophoretic field of about 350 V/cm. Fluorescence image shown in FIG. 3A was taken after an elapsed separation time of 16 seconds after launching the sample from the sample reservoir loading area into a 6% polyacrylamide gel. In each sample, TTC* was used as the fluorescently labeled antigen and anti-TTC antibodies were used as the analyte. Detection of a second peak, having a lower apparent mobility than the mobility of free TTC*, indicates formation of a (fluorescent) TTC*-immune complex (Ab-TTC*); as the relative magnitudes of the TTC* and Ab-TTC* peaks are directly related to the antibody concentration. As the amount of unlabeled TTC is increased, the intensity of the TTC* band decreases with a concomitant intensity increase in the immune complex band.

Figure 3A:
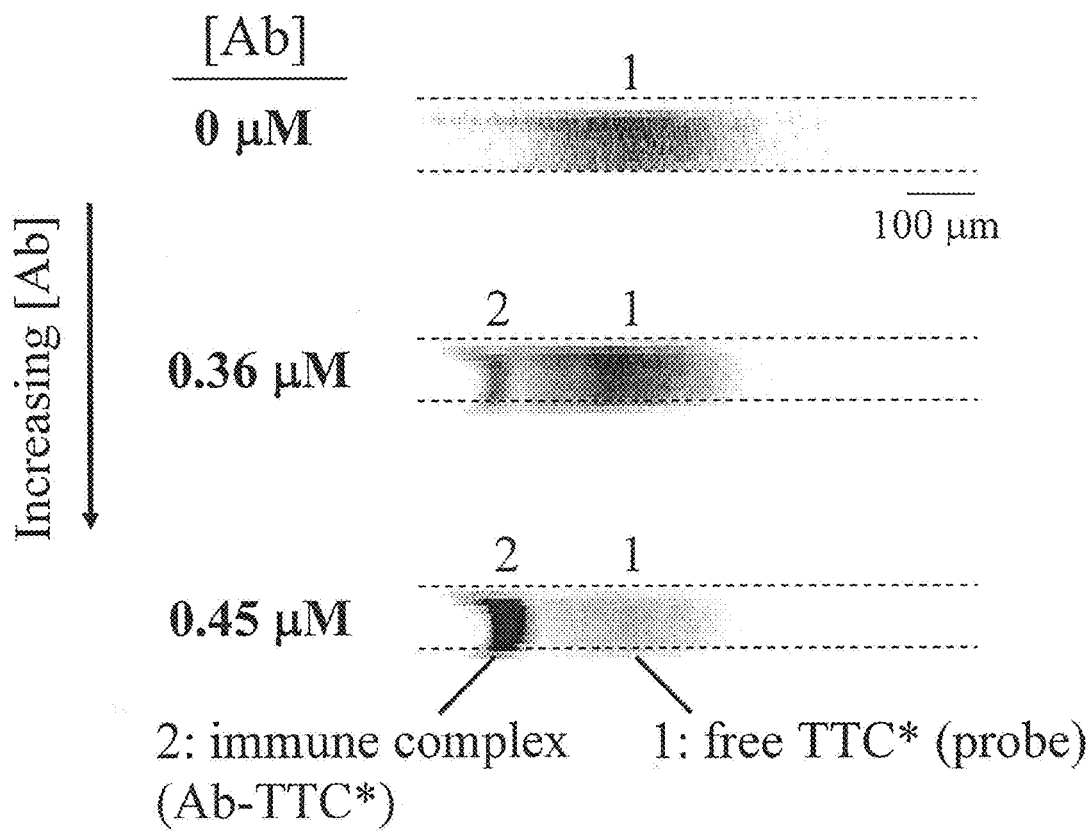
FIG. 3A shows an inverted grayscale digital image of a 16 second on-chip PAGE direct immunoassay in a 6% total acrylamide gel+1×Tris-glycine run buffer (pH 8.3) for detection of anti-TTC antibodies present in the sample.

As shown in FIG. 3A, the immune complex is nearly resolved from the free TTC* in less than 30 seconds and in a 7 mm long separation distance. By way of comparison, capillary zone electrophoresis-based immunoassays have been reported to complete in 2 to 3 minutes when using Fab antibody fragments (13 minutes when using the whole antibody), while on-chip free solution electrophoresis immunoassays have been reported complete in less than 40 seconds.

Quantitation of electropherogram peak height and peak area was employed to generate dose-response curves for the tetanus system. To do this, the peak area corresponding to the immune complex was normalized by the peak area of the free dye internal standard, associated with the fluorescent labeling of the analyte and proportional in concentration to the amount of labeled analyte in the sample, to correct for variation in the injected sample volume, as well as for any uncorrected variations in excitation illumination. Furthermore, the minimum detectable concentration (MDC) of immune complex Ab-TTC was defined as the lowest concentration of analyte (anti-TTC antibody) that resulted in a fluorescence signal response three standard deviations higher than the response at zero concentration. For the LIF/PMT system described above, this concentration was found to be an MDC of $6.8 \times 10^{-10}$ M of unlabeled anti-TTC antibody which compares favorably with reported detection limits of $10^{-12}$ M to $10^{-9}$ M for conventional immunoassay methods (e.g., enzyme-linked immunosorbent assays). As noted earlier, the amount of free TTC* and the concentration of the internal standard in each of the initially prepared sample mixtures was held constant.

Figure 3B:
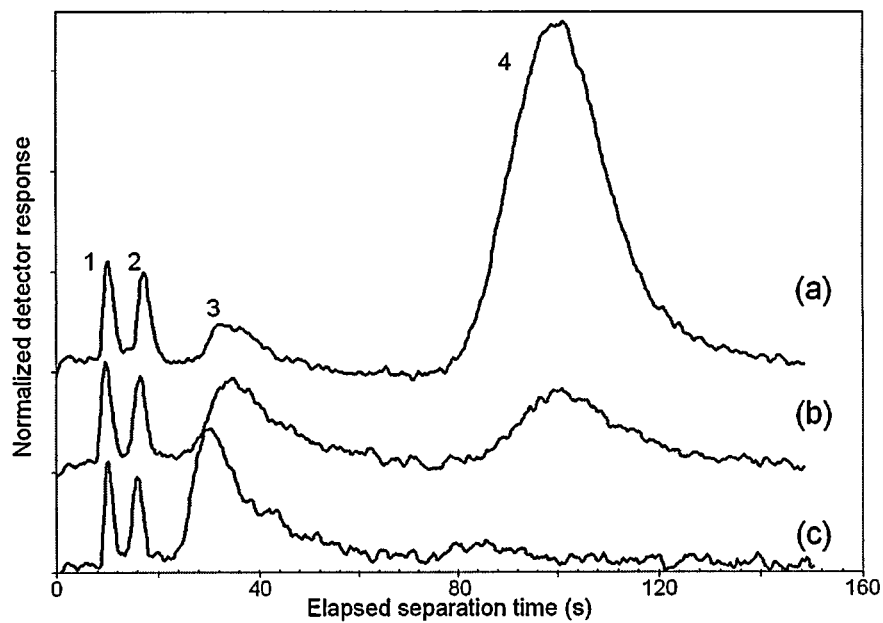
FIG. 3B shows a series of electropherograms obtained from on-chip direct immunoassays containing a constant TTC* (fluorescently labeled TTC) concentration of $13\times10^{-9}$ M with decreasing anti-TTC antibody concentration values of: (a) $5.4\times10^{-9}$ M, (b) $1.4\times10^{-9}$ M, (c) $0.2\times10^{-9}$ M, wherein peaks 1 and 2 correspond to free dye and are used as a standard, peak 3 is the free TTC*, and peak 4 is the fluorescent immune complex (Ab-TTC*).

As illustrated in FIGS. 3A and 3B, single point detection measurements yielded electropherograms for the native PAGE immunoassay of low concentration TTC* samples. Just as in the full-field images shown in FIG. 3A, the peak associated with the immune complex is clearly observable as the concentration of anti-TTC antibodies increased from 0.2× $10^{-9}$ M to $5.4 \times 10^{-9}$ M. Moreover, separation of the immune complex from free TTC* is complete within about 150 seconds using the single point method.

FIG. 3B shows a series of electropherograms obtained from on-chip direct immunoassays containing a constant TTC* concentration of $13 \times 10^{-9}$ M with decreasing anti-TTC antibody concentration values of: (a) $5.4 \times 10^{-9}$ M, (b) $1.4 \times 10^{-9}$ M, (c) $0.2 \times 10^{-9}$ M. In FIG. 3B, peaks 1 and 2 correspond to free dye and are used as a normalizing standard, peak 3 is the free TTC*, and peak 4 is the fluorescent immune complex. Moreover, while only the peaks 1-4 are labeled for curve (a), the corresponding peaks are clearly visible in both of curves (b) and (c) with the exception of peak 4 in curve (c).

Figure 4:
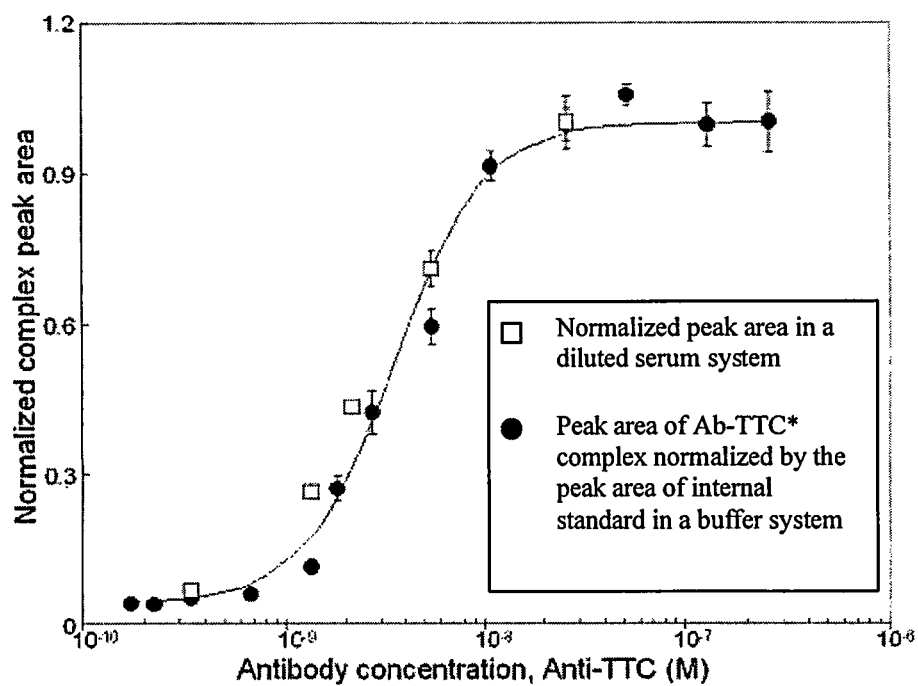
FIG. 4 illustrates a dose-response curve for TTC* by on-chip PAGE direct immunoassay. Filled data points correspond to the peak area of the TTC fluorescent immune complex (Ab-TTC*) complex normalized by the peak area of internal standard in a buffer system, while unfilled points correspond to normalized peak area in a diluted serum system.

FIG. 4 shows the dose-response curve for the measurement of anti-TTC antibody by direct immunoassay. In these experiments, the TTC* concentration was held constant at $13.0 \times 10^{-9}$ M, while the concentration of anti-TTC antibody was varied. The data in FIG. 4 was fit using a four parameter logistic model of the form:

$$F = \beta_2 + \frac{(\beta_1 - \beta_2)}{1 + ([Ab]/\beta_3)^{\beta_4}},$$

where F and [Ab] are the normalized peak area and anti-TTC antibody concentration, respectively, where $\beta_1$ is the asymptote as $[Ab] \to 0$, $\beta_2$ is the asymptote as $[Ab] \to \infty$, $\beta_3$ is the logarithm of the predicted peak area at the response midpoint (halfway between the two peak area asymptotes), and $\beta_4$ is the Hill coefficient, which is related to the steepness of the sigmoidal dose-response curve. In this case, the best nonlinear, least-squares fit to the data were obtained using the parameter values: $\beta_1 = 0.04$, $\beta_2 = 1.0$, $\beta_3 = 3.5 \times 10^{-9}$, and $\beta_4 = 1.9$.

The effects of interfering substances on the ability of the immunoassay to accurately determine the quantity of tetanus antibody in biological specimens was determined by measuring the normalized peak areas for direct anti-TTC antibody immunoassays conducted in a 1/100 diluted bovine serum specimen containing $13 \times 10^{-9}$ M of TTC* (indicated by open or "hollow" data symbols). FIG. 4 shows the normalized peak area measurements from the adulterated (dilute serum) specimen in comparison to the results from the buffer-based immunoassay. Peak areas for both the buffer and diluted serum immunoassays were normalized to the $\beta_2$ value for each dose-response curve. The peak area measurements from the diluted serum sample can be described by the same four-parameter model used to generate the dose-response curve obtained in buffer solutions.

Example 2

On-Chip Competitive Immunoassay for TTC

In addition to direct immunoassays, competitive format immunoassays for tetanus toxin C-fragment were performed in the photopatterned cross-linked gels. Sample solutions consisting of TTC*, TTC, and anti-TTC antibodies again having known concentrations were prepared in 1x native Tris-glycine buffer off-chip. The molar ratio of TTC* to anti-TTC antibody, as well as the final sample volume, was kept constant for all competitive samples. The concentration of unlabeled TTC added to the sample solutions was varied to obtain the desired final unlabeled TTC concentration. In all cases, anti-TTC antibody was the final component added to the competitive sample solutions. Incubation conditions were as described above for the direct immunoassays.

Figure 5A:
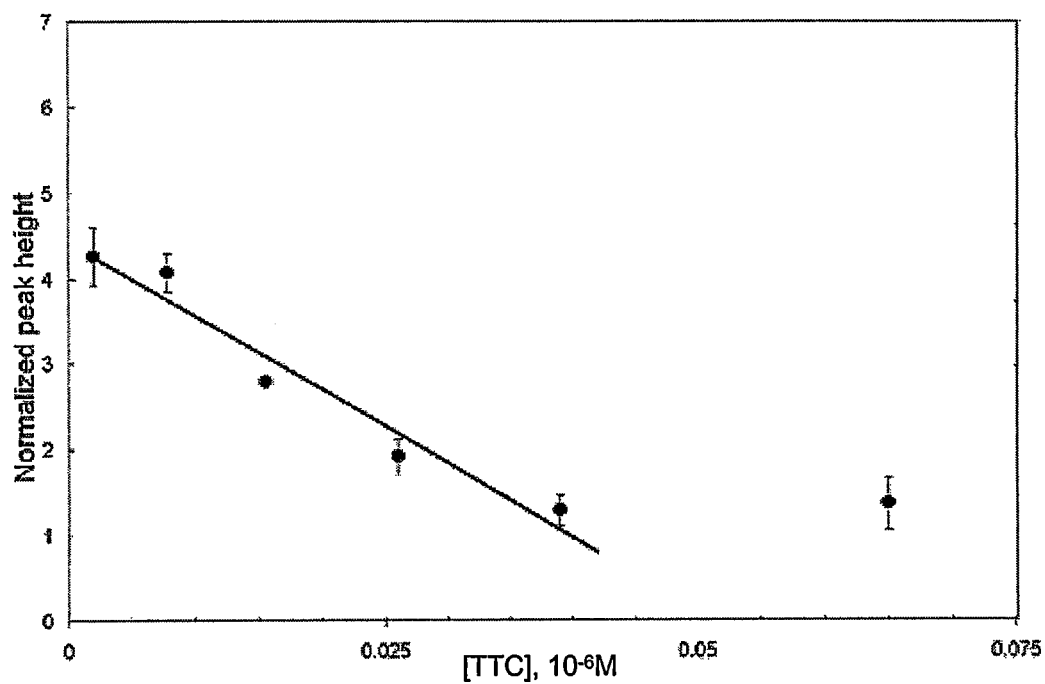
FIG. 5A shows a dose-response curve for TTC* by on-chip competitive PAGE immunoassays corresponding to the electropherograms of FIG. 5B. Filled data points correspond to the peak height of the Ab-TTC* complex normalized by the peak height of the free dye.
Figure 5B:
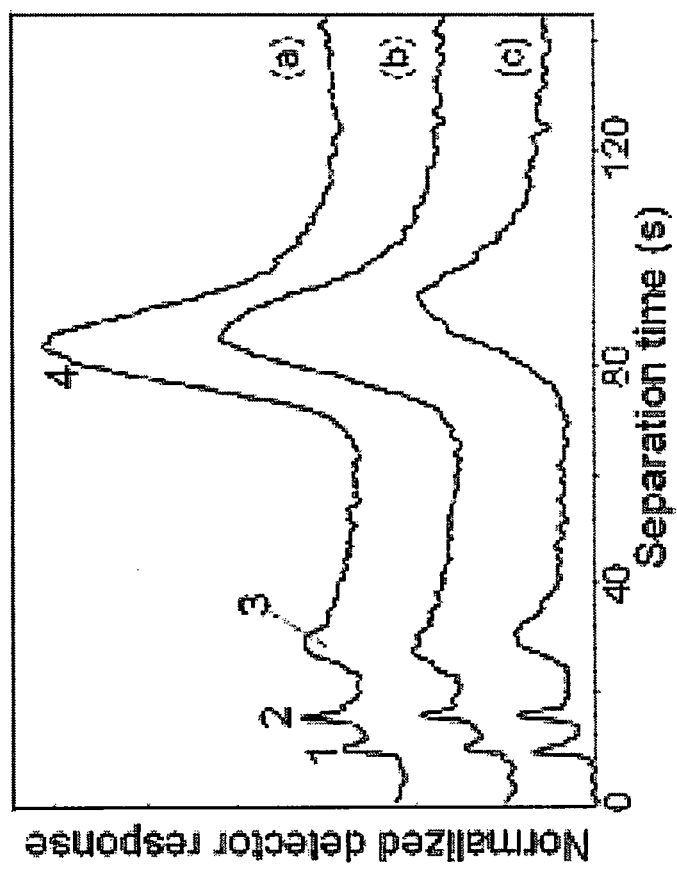
FIG. 5B illustrates a series of electropherograms for an on-chip competitive immunoassay wherein TTC* ($13\times10^{-9}$ M) and anti-TTC antibody ($6\times10^{-9}$ M) concentrations are held constant while unlabeled TTC concentrations are: (a) $2.0\times10^{-9}$ M, (b) $7.8\times10^{-9}$ M, and (c) $15.6\times10^{-9}$ M, wherein peaks 1 and 2 correspond to free dye (peak 2 used a standard), peak 3 is the free TTC*, and peak 4 is the complex.

As conducted, the competitive immunoassays were designed to use TTC* as a fluorescently labeled antigen reporter and TTC as analyte, both of which compete to form complexes with the anti-TTC antibodies. FIG. 5A shows the dose-response curve for the competitive immunoassay where the detector response was normalized to the internal standard (peak 2), and where E=300 V/cm, where the total column length was 6.1 cm. FIG. 5B shows representative electropherograms from a competitive immunoassay having constant concentrations of TTC* ($13 \times 10^{-9}$ M) and anti-TTC antibodies ($6 \times 10^{-9}$ M) and TTC concentrations of 2.0, 7.8, and $15.6 \times 10^{-9}$ M. Peaks 1 and 2 correspond to free dye (peak 2 used a standard), peak 3 is the free TTC*, and peak 4 is the complex.

Competitive immunoassays rely upon competition between fluorescently labeled antigen and unlabeled sample antigen to form an immune complex with the unlabeled antibody (or antibody fragment). Quantitation of either the labeled antigen peak or the fluorescent immune complex peak should ideally allow determination of the amount of unlabeled antigen present in a given sample. As is seen in FIG. 5B, the fluorescent complex peak (peak 4) height diminishes as TTC is added to the sample with a concomitant increase in the peak height of the free TTC* (peak 3). These observations are indicative of expected competitive immunoassay behavior, wherein an increase in sample antigen concentration results in both an increase in observed free labeled antigen and decrease in the observed fluorescent immune complex, as the sample antigen antibody immune complex is not fluorescent. Eventually, as the concentration of TTC is increased, nonlinearity is observed in the dose-response curve of FIG. 5A and is presumably indicative of saturation of the anti-TTC antibodies with TTC.

Native PAGE separations of proteins and immune complexes have been demonstrated, therefore, in an in situ photopatterned separation medium of cross-linked polyacrylamide gels. Analysis of model proteins using native PAGE allowed extraction of retardation coefficients based upon measured apparent mobilities of each analyte in gels of various total acrylamide concentrations. A dose-response curve for the direct immunoassay for antibodies to tetanus toxin C-fragment was generated and showed limiting behaviors expected of conventional direct immunoassays, as quantified through a four-parameter logistic model. Furthermore, direct immunoassays for antibodies to tetanus toxin performed in a diluted serum solution also agreed with trends anticipated from a conventional immunoassay format. The minimum detectable antibody concentration was measured to be $6.8 \times 10^{-10}$ M. The microsystem was extended to include a competitive immunoassay for tetanus toxin C-fragment, which resulted in generation of an additional dose-response curve. Both direct and competitive immunoassays were completed with separation times of less than three minutes.

Example 3

Detection of TNFa in Saliva

Figure 6A:
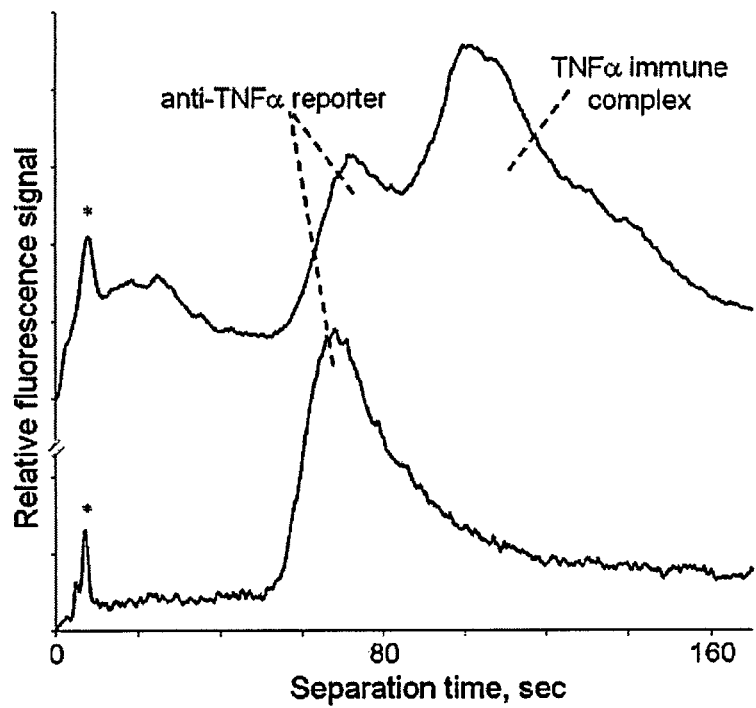
FIG. 6A shows electrophoresis-based immunoassay results in diluted (1:1 in buffer) whole saliva for detection of tumor necrosis factor alpha (TNFa).

FIG. 6A shows electrophoresis-based immunoassay results in diluted (1:1 in buffer) whole saliva for detection of tumor necrosis factor alpha (TNFa). The top-most electropherogram shows assay results for a healthy saliva sample spiked with TNFa (spiked at a concentration of 130 nM), while the bottom electropherogram shows the immunoassay results for a healthy saliva sample containing only the anti-TNFa reporter (at a concentration of 250 nM). An asterisk marks an internal standard, while both the anti-TNFa reporter (the fluorescently-labeled antibody) and immune complex are labeled. Assays shown were conducted in a 6% gel (acrylamide:bis-acrylamide=37.5:1) that employed 0.2% photoinitiator. A photomultiplier tube collected fluorescence intensity information at a location 3 mm from the loading region. The applied electric field was 350 V/cm. The gel buffer was Tris-glycine (pH=8.9) devoid of sodium dodecyl sulfate. The antibody (US Biological, Swampscott, Mass.) was fluorescently-labeled using ALEXA FLUOR® 647 (Molecular Probes, Eugene Oreg.). While not baseline resolved, the reporter and immune complex peaks are discernable in FIG. 6A, indicating that it is possible to detect the cytokine TNFa in spiked human saliva in less than about three minutes over a distance of about 3 mm.

Figure 6B:
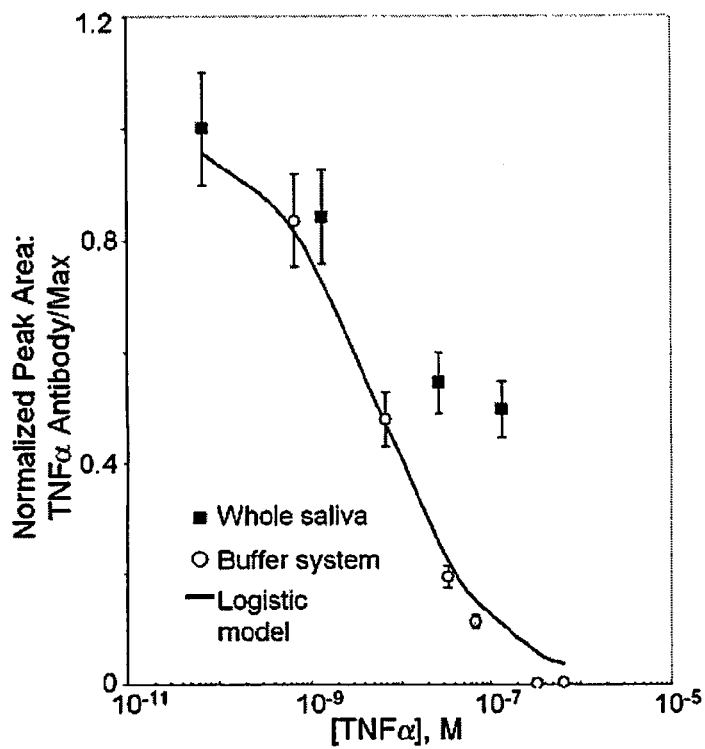
FIG. 6B shows an immunoassay calibration curve developed for this assay in both spiked buffer and spiked healthy human saliva.

FIG. 6B shows an immunoassay calibration curve developed for this assay in both spiked buffer and spiked healthy human saliva. Assay results show the ability to detect the TNFa cytokine over an abundance range spanning three-orders of magnitude (from $10^{-7}$ to $10^{-10}$ M). The calibration curve was generated using assays similar to that shown in FIG. 6A, wherein peak area information was extracted regarding the anti-TNFa reporter peak at a variety of TNFa concentrations. Error bars are based upon run-to-run error and reflect the precision of the assay.

Example 4

Detection of IL-6 in Saliva

Figure 7A:
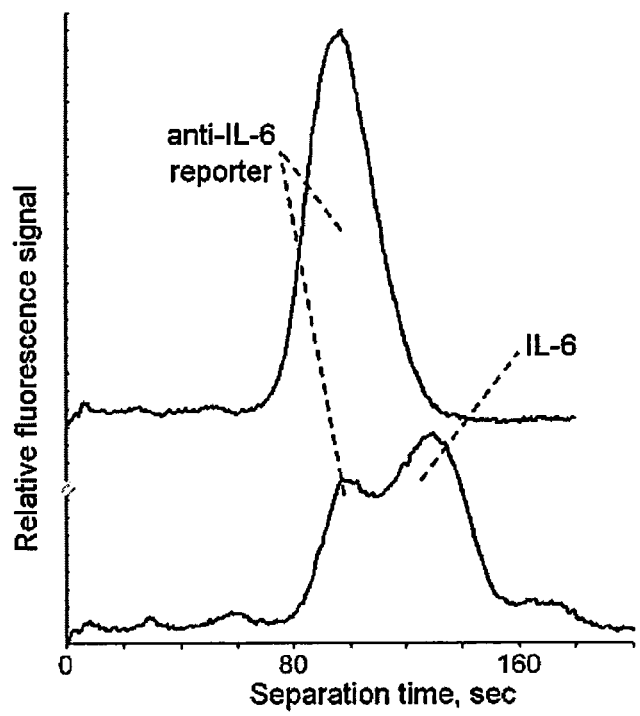
FIG. 7A shows electrophoresis-based immunoassay results in diluted (1:1 in buffer) whole saliva for detection of interleukin-6 (IL-6).

FIG. 7A shows electrophoresis-based immunoassay results in diluted (1:1 in buffer) whole saliva for detection of interleukin-6 (IL-6). The bottom-most electropherogram shows assay results for a healthy saliva sample spiked with IL-6 (spiked at a concentration of 8 nM), while the top electropherogram shows the immunoassay results for a healthy saliva sample containing only the anti-IL-6 reporter (at a concentration of 100 nM). An asterisk marks an internal standard, while both the anti-IL-6 reporter (the fluorescently-labeled antibody) and immune complex are labeled. Assays shown were conducted in a 6% gel (acrylamide:bis-acrylamide=37.5:1) that employed 0.2% photoinitiator. A photomultiplier tube collected fluorescence intensity information at a location about 3 mm from the loading region. The applied electric field was 350 V/cm. The gel buffer was Tris-glycine (pH=8.9) devoid of sodium dodecyl sulfate. The antibody (US Biological, Swampscott, Mass.) was fluorescently labeled using ALEXA FLUOR® 647 (Molecular Probes, Eugene, Oreg.). While not baseline resolved, the reporter and immune complex peaks are discernable in FIG. 7A, indicating that it is possible to detect the cytokine IL-6 in spiked human saliva in less than about two minutes over a distance of about 3 mm.

Figure 7B:
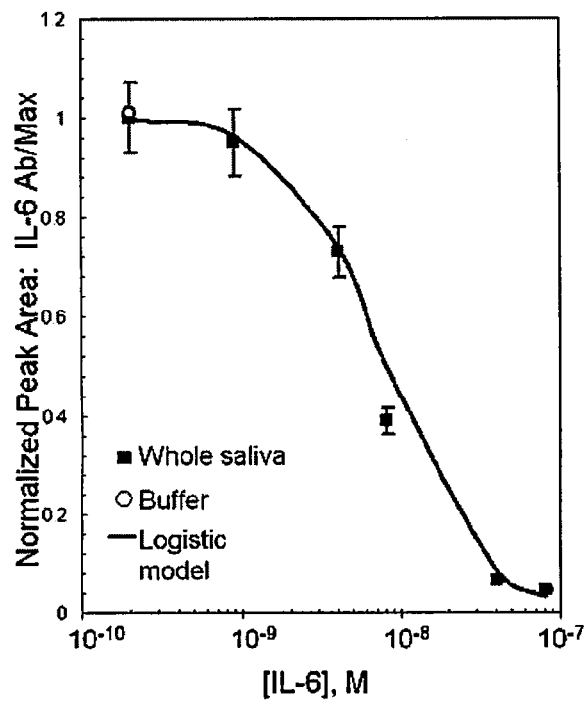
FIG. 7B shows an immunoassay calibration curve developed for this assay in "spiked" healthy human saliva.

FIG. 7B shows an immunoassay calibration curve developed for this assay in "spiked" healthy human saliva. Assay results show the ability to detect the IL-6 cytokine over an abundance range spanning two-orders of magnitude (from $10^{-7}$ to $10^{-9}$ M). The calibration curve was generated using assays similar to that shown in FIG. 7A, wherein peak area information was extracted regarding the anti-IL-6 reporter peak at a variety of IL-6 concentrations. Error bars are based upon run-to-run error and reflect the precision of the assay.

Example 5

Detection of C-RP in Saliva

Figure 8A:
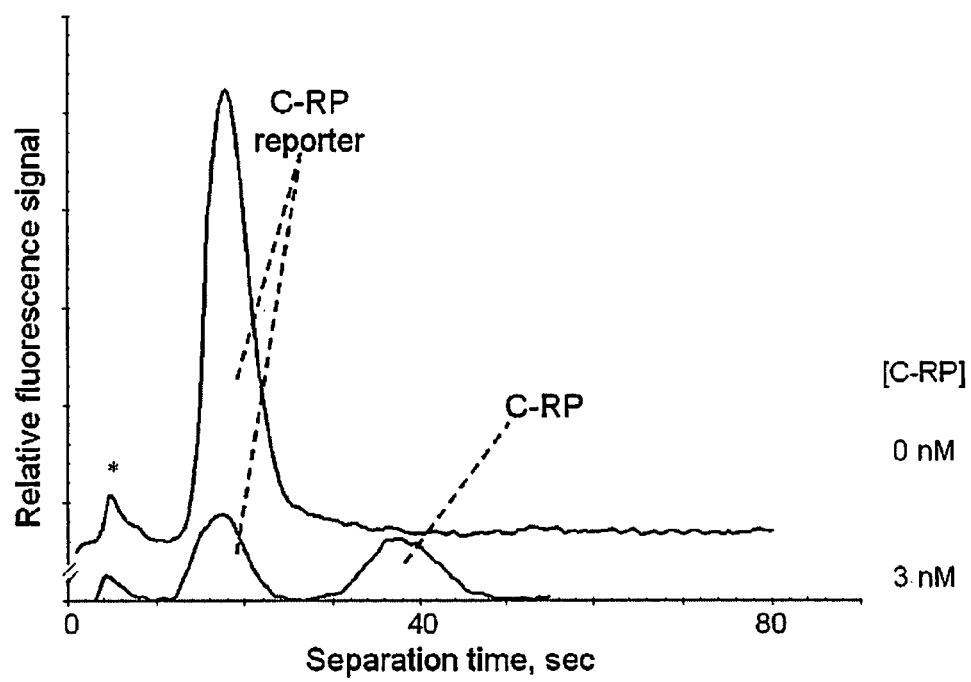
FIG. 8A shows electrophoresis-based immunoassay results in diluted (1:1 in buffer) whole saliva for detection of C-reactive protein (C-RP).

FIG. 8A shows electrophoresis-based immunoassay results in diluted (1:1 in buffer) whole saliva for detection of C-reactive protein (C-RP). The bottom-most electropherogram shows assay results for a healthy saliva sample spiked with C-RP (spiked at a concentration of 3 nM), while the top electropherogram shows the immunoassay results for a healthy saliva sample containing only the anti-C-RP reporter (at a concentration of 100 nM). An asterisk marks an internal standard, while both the anti-C-RP reporter (the fluorescently-labeled antibody) and immune complex are labeled. Assays shown were conducted in a 6% gel (acrylamide:bis-acrylamide=37.5:1) that employed 0.2% photoinitiator. A photomultiplier tube collected fluorescence intensity information at a location 3 mm from the loading region. The applied electric field was 350 V/cm. The gel buffer was Tris-glycine (pH=8.9) devoid of sodium dodecyl sulfate. The antibody (US Biological, Swampscott, Mass.) was fluorescently-labeled using ALEXA FLUOR® 647 (Molecular Probes, Eugene, Oreg.). The baseline-resolved reporter and immune complex peaks are discernable in FIG. 8A, indicating that it is possible to detect the C-RP in spiked human saliva in less than about one minute over a distance of about 3 mm.

Figure 8B:
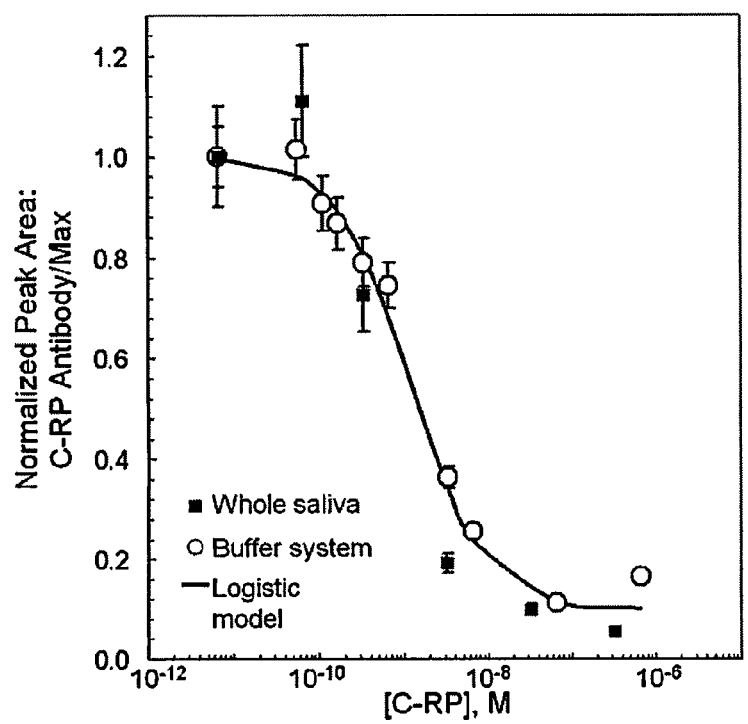
FIG. 8B shows an immunoassay calibration curve developed for this assay in both spiked buffer and spiked healthy human saliva.

FIG. 8B shows an immunoassay calibration curve developed for this assay in both spiked buffer and spiked healthy human saliva. Assay results show the ability to detect the C-RP over an abundance range spanning three-orders of magnitude (from $10^{-7}$ to $10^{-10}$ M). The calibration curve was generated using assays similar to that shown in FIG. 8A, wherein peak area information was extracted regarding the anti-C-RP reporter peak at a variety of C-RP concentrations. Error bars are based upon run-to-run error and reflect the precision of the assay.

Figure 8C:
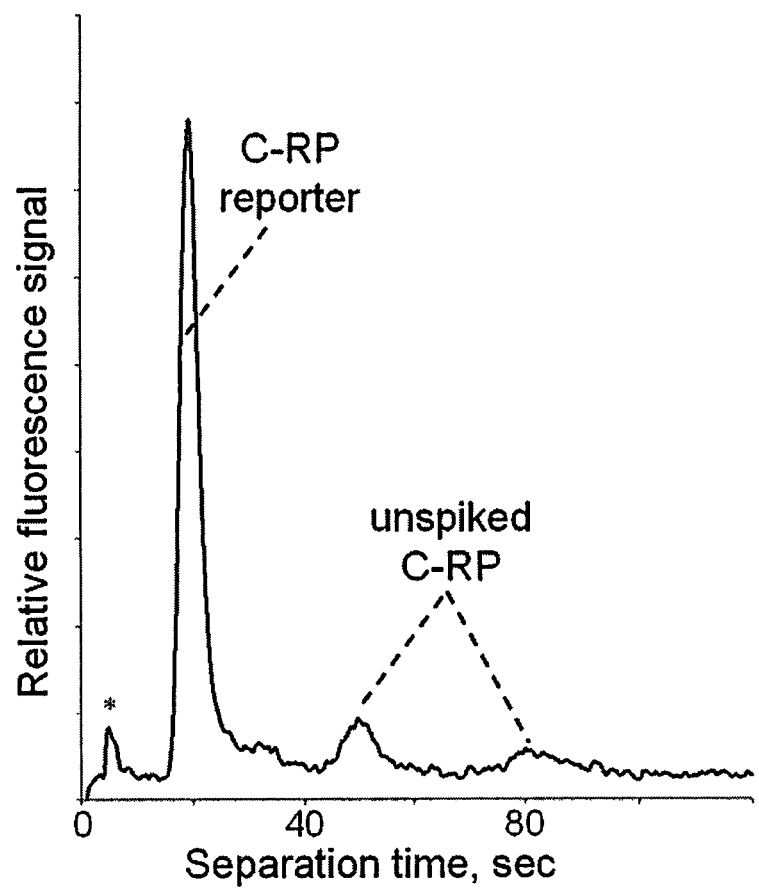
FIG. 8C shows electrophoresis-based immunoassay results in diluted albumin-depleted unspiked human serum for detection of C-reactive protein (C-RP).

FIG. 8C shows electrophoresis-based immunoassay results in diluted albumin-depleted unspiked human serum for detection of C-RP. An asterisk marks an internal standard, while both the anti-C-RP reporter (the fluorescently-labeled antibody) and immune complex are labeled. Assays shown were conducted in a 6% gel (acrylamide:bis-acrylamide=37.5:1) that employed 0.2% photoinitiator. A photomultiplier tube collected fluorescence intensity information at a location about 3 mm from the loading region. The applied electric field was 350 V/cm. The gel buffer was Tris-glycine (pH=8.9) devoid of sodium dodecyl sulfate. The antibody (US Biological, Swampscott, Mass.) was fluorescently-labeled using ALEXA FLUOR® 647 (Molecular Probes, Eugene, Oreg.). The baseline-resolved reporter and immune complex peaks are discernable in FIG. 8C, indicating that it is possible to detect the C-RP in unspiked human serum in less than about two minutes over a distance of about 3 mm.

The direct and competitive immunoassays reported illustrate the simplicity, speed, and quantization associated with on-chip electrophoresis-based immunodiagnostics. Other embodiments are possible including combining the assay with on-chip mixing and metering, extension of the system to include multi-analyte detection in a parallel separation format, and enhanced automation will enable high-throughput analysis of complex samples devoid of user intervention.

In particular, the invention may be deployed in kit form by providing, as separate packages A) a microfluidic separation system is first provided on a substrate such as glass, silicon, polysilicon, quartz, or similar material. The separation system itself would include as a minimum, i) at least one capillary separation channel disposed on the substrate, wherein the separation channel contains a porous polymerized polyacrylamide gel as described above; ii) at least one fluid reservoir intersecting with the separation channel, wherein the separation channel and the fluid reservoir contain a buffer fluid; and iii) electrodes for electrically connecting the fluid reservoirs and channels to an external power supply; and B) several sterile containers each containing a different antibody capable of immunoreacting with a different target antigen, wherein each antibody is labeled with a reporter molecule such as a fluorophore.

The microfluidic diagnostic kit would be remain sealed until use and would be used by first mixing a small quantity of a body fluid/component with the same type of buffer fluid used in the kit. Labeled receptor molecules (e.g., fluorescently-labeled antibodies with specificity for the analyte of interest) are incubated with the body fluid as described above in the preceding text. A quantity of the fluorophore is also added as an internal standard. (The process may be practiced also by introducing the tagged antigen mixture and the antibody directly into the reservoir of the microfluidic chip and incubating the analyte sample on the chip itself thereby reducing one of the handling steps.)

After incubating the analyte sample(s) as described above an individual sample is injected into the reservoir on the separation channel system, electrophoretically separated, stimulated by exposure to an excitation source (e.g., laser, Hg-lamp), and any induced fluorescent signal recorded electronically. This process is repeated for each analyte sample. Based upon measured calibration curves, an estimate of the concentration of the analyte of interest can be made for each body fluid analyzed.

Alternatively, incubation may be performed "on-chip." Analyte-containing sample and receptor containing solutions must be mixed to allow binding of the analyte to the receptor molecule. This can require substantial incubation times on the macroscale (i.e., in vitro). Using micron-scale channels or compartments as mixing regions, even when relying solely on diffusion to transport the species, can result in efficient mixing of the various species. The reduced distances involved in such a mixing system reduce the amount of time necessary to complete the mixing process, even under laminar flow conditions.

Figure 9:
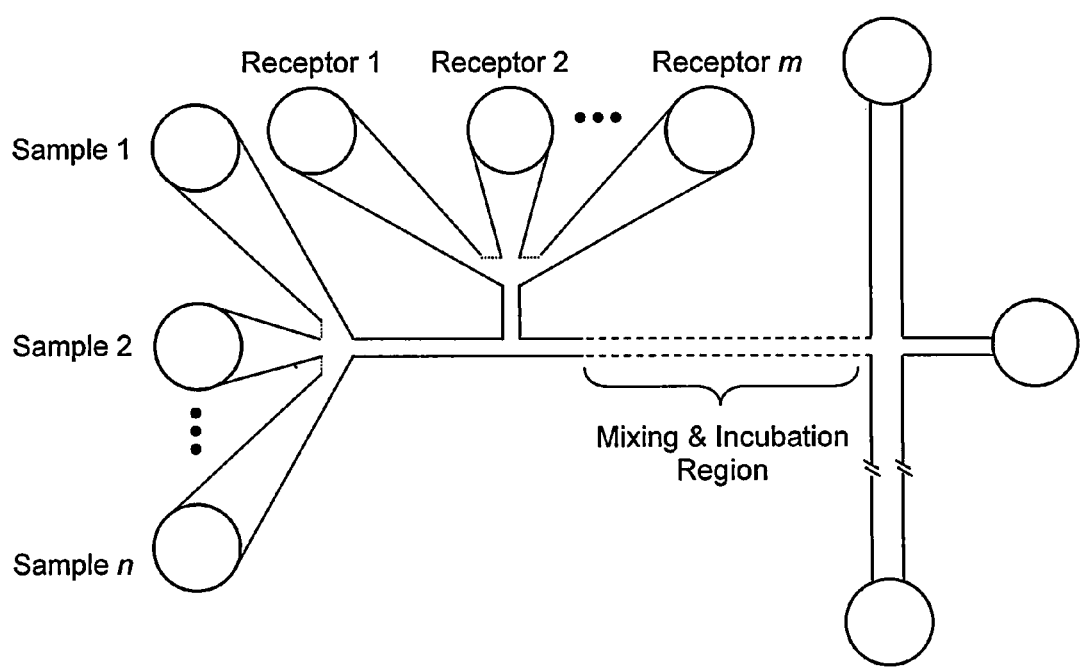
FIG. 9 shows a cartoon of an "on-chip" microdevice having multiple sample and receptor reservoirs connected to a pre-separation mixing region which doubles as an incubation region within the device.

Prior to gel electrophoresis immunoassay analysis, sample species can be mixed with either a single receptor or multiple receptors for determination of analyte presence in a particular sample. Using a microfabricated device, such as is shown in FIG. 9, all of the upstream mixing and metering can take place prior to analysis in a single device. Samples are introduced, either electrokinetically or using pressure-driven flow, into a region of the device where they are substantially brought into contact with one or more reporter molecules. A region of the device, prior to electrophoretic analysis in the polyacrylamide gel, allows incubation and mixing of the analyte-containing sample and receptor molecules. The mixing and incubation region of the device may be a straight channel, a serpentine mixing channel, a multi-level mixing channel, or any of a number of other geometries. In addition to a continuous pressure-driven or electrokinetic flow, a stopped-flow protocol may be employed, wherein species are allowed to incubate and mix without the presence of a net flow.

Finally, to the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for preparing a separation system for electrophoretically separating chemical and/or biological species, comprising:
    providing a capillary separation channel disposed on a substrate, comprising:
        a fluid reservoir disposed at each of first and second ends of the capillary separation channel, wherein the fluid reservoirs and the capillary separation channel filled with a first solution mixture comprising an acrylamide monomer, a bis-acrylamide monomer, and a UV photoinitiator having a first predetermined concentration of total acrylamide;
        a mixing and incubation region proximal to the first end of the capillary separation channel; and
        a plurality of adjacent side channels each having at least one fluid reservoir in fluid communication with the side channel, wherein each of the at least one fluid reservoirs contains a quantity of one of a plurality of second solution mixtures, wherein each of the second solution mixtures again comprises an acrylamide monomer, a bis-acrylamide monomer, and a UV photoinitiator and wherein each of the second solution mixtures comprise a plurality of predetermined concentrations of total acrylamide which may be the same or different than the first predetermined concentration;
    introducing a measured portion of the second solution mixtures contained within two or more of the side channels reservoirs into the capillary separation channel until each of the solution mixtures contacts an adjacent solution mixture along a contact interface;
    mixing each of the plurality of first and second solution mixtures within the capillary separation channel by diffusion for a period of time;
    simultaneously exposing the mixed solution mixtures within the capillary separation channel to a quantity of UV light polymerizing the mixed solution mixture and thereby providing a length of polyacrylamide gel having a gradient in total acrylamide concentration; and
    providing a programmable high voltage power supply in electrical communication with the first and second ends of the capillary separation channel, the high voltage power supply providing an electric field within each of the capillary separation channels, wherein the electric field and the depth and width of the capillary separation channels cooperate to provide electrophoretic separation of a species complex introduced into the capillary separation channel in less than about 60 seconds.

2. A microfluidic separation system for electrophoretically separating trace species, comprising:
    two or more capillary separation channels disposed on a substrate, wherein each of the two or more capillary separation channels comprise;
        a fluid reservoir at first and second ends of each of the two or more capillary separation channels;
        a mixing and incubation region proximal to the first end of each of the two or more capillary separation channels;
        a length of about 67 mm or less;
        a depth and width of about 40 µm and 100 µm, respectively; and
        a polymerizable solution comprising an acrylamide monomer, a bis-acrylamide monomer, and a UV photoinitiator, wherein the polymerizable solution within each of the two or more capillary separation channels is the same or is different and wherein the polymerizable solution is selected to provide a step-wise or continuous gradient of concentrations between about 0% to about 15% total acrylamide along the length of the each of the two or more capillary separation channels;
    a programmable high voltage power supply in electrical communication with electrodes inserted into each of the fluid reservoirs; and
    a high voltage electric field between the first and second ends of each of the two of more capillary separation channels, wherein the electric field and the depth and width of each of the two of more capillary separation channels cooperate to provide electrophoretic separation of a species complex introduced therein in less than about 60 seconds.

3. A microfluidic separation system for electrophoretically separating trace species, comprising: a capillary channel disposed on a substrate comprising:
    (i) first and second ends;
    (ii) at least one analyte inlet reservoir in fluid communication with the first end;
    (iii) a fluid reservoir in fluid communication with the second end;
    (iv) a mixing and incubation region proximal to the first end and comprising a length of straight channel, length of serpentine channel, a length of multi-level mixing channel, or other geometries;
    (v) a separation region adjacent to and in fluid communication with the mixing region, the separation region disposed between the mixing region and the second end of the capillary channel, the separation region comprising a polymerizable solution comprising an acrylamide monomer, a bis-acrylamide monomer, and a UV photoinitiator, wherein the polymerizable solution is selected to provide a step-wise or continuous gradient of concentrations between about 0% to about 15% total acrylamide along the length of the capillary separation channel;

a side channel having first and second ends, at least one receptor inlet reservoir in fluid communication with the first end, wherein the side channel second end intersects and opens into the capillary channel at a point between the capillary channel first end and the mixing region, wherein the side channel is in fluid communication with the capillary channel;

a programmable high voltage power supply in electrical communication with electrodes inserted into each of the fluid reservoirs;

a high voltage electric field between the first and second ends of the capillary channel, wherein the electric field and the depth and width of the capillary channel cooperate to provide electrophoretic separation of an analyte species introduced therein in less than about 60 seconds.

4. The microfluidic separation system of claim 2 or 3, wherein the step gradient comprising 3 or more steps.

5. The microfluidic separation system of claim 2 or 3, wherein polymerizable gradient comprises acrylamide concentrations between about 3% to about 15% total acrylamide.

* * * * *